(12) United States Patent
Dermatakis et al.

(10) Patent No.: US 7,112,676 B2
(45) Date of Patent: Sep. 26, 2006

(54) PYRIMIDO COMPOUNDS HAVING ANTIPROLIFERATIVE ACTIVITY

(75) Inventors: Apostolos Dermatakis, Parlin, NJ (US); Marek Michal Kabat, Nutley, NJ (US); Kin-Chun Luk, North Caldwell, NJ (US); Pamela Loreen Rossman, Nutley, NJ (US); Sung-Sau So, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 154 days.

(21) Appl. No.: 10/689,235

(22) Filed: Oct. 20, 2003

(65) Prior Publication Data

US 2005/0075272 A1 Apr. 7, 2005

Related U.S. Application Data

(60) Provisional application No. 60/423,670, filed on Nov. 4, 2002.

(51) Int. Cl.
*C07D 487/04* (2006.01)
*A61K 31/519* (2006.01)
*A61P 35/00* (2006.01)

(52) U.S. Cl. .................. 544/256; 544/326; 544/334; 514/262.1

(58) Field of Classification Search ............... 544/256, 544/326, 334; 514/262.1
See application file for complete search history.

(56) References Cited

U.S. PATENT DOCUMENTS

| | | | |
|---|---|---|---|
| 2,949,466 | A | 8/1960 | Hoefle et al. |
| 3,939,084 | A | 2/1976 | Sullivan |
| 4,425,346 | A | 1/1984 | Horlington |
| 4,886,807 | A | 12/1989 | Kitamura et al. |
| 6,150,373 | A | 11/2000 | Harris et al. |
| 6,451,804 | B1 | 9/2002 | Dunn et al. |
| 2004/0019210 | A1 | 1/2004 | Connolly et al. |
| 2004/0097485 | A1 | 5/2004 | Burkitt et al. |

FOREIGN PATENT DOCUMENTS

| | | |
|---|---|---|
| WO | WO 98/24432 | 6/1998 |
| WO | WO 99/61444 | 12/1999 |
| WO | WO 00 24744 | 5/2000 |
| WO | WO 01/29041 | 4/2001 |
| WO | WO 01/29042 | 4/2001 |
| WO | WO 01/64679 | 9/2001 |
| WO | WO 02/18380 A1 | 3/2002 |
| WO | WO 03/062236 | 7/2003 |

OTHER PUBLICATIONS

Draetta, G. and Pagano, M. in "Annual Reports in Medicinal Chemistry, vol. 31", 1996, Academic Press, San Diego, p. 241-248.*

Noble, M.E.M. et al, Science, vol. 303, 2004, pp. 1800-1805.*
Anderson, M.R. et al, Expert Opin. Investig. Drugs, 2003, 12(4) 577-592.*
Laird, A.D. et al, Expert opin. Investig. Drugs, 2003, 12(1), 51-64.*
Traxler, Peter, Expert Opin. Ther. Targets, 2003, 7(2) 215-234.*
Hennequin L. F. et al., J. Med. Chem. 2002, vol. 45(6) pp. 1300-1312.
Klohs W. E. et al., Current Opinion in Biotechnology, 1999 vol. 10, pp. 544-549.
D. H. Boschelli & F. Boschelli, Drugs of the Future, 2000 25(7) pp. 717-736.
Ansel, H. et al., *Pharmaceutical Dosage Forms & Drug Delivery Systems* 6th Ed. 1995, p. 196.
J. Alexander, et al., *J. Med. Chem. 1988*, vol. 31, pp. 318-322.
Masquelin et al., *Helvetica Chimica Acta*, vol. 81 (1998) pp. 646-659.
Devi, et al., *Indian Journal of Heterocyclic Chemistry*, vol. 7, Jan.-Mar. 1998, pp. 193-196.
Tominaga et al., *Chemical & Pharmaceutical Bulletin*, vol. 32, No. 1, Jan. 1984, pp. 122-129.
Tominaga et al., *Heterocycles*, vol. 12, No. 4. 1979, pp. 503-504.
Marsh et al., *Chemical Communications*, 1996, pp. 1527-1528.
*Z. Chem.* 20 Jg (1980) Heft. 11, pp. 412-413.
Cappuccino et al., *Cancer Research*, vol. 24, Aug. 1964, pp. 1243-1248.
Chatterjee et al., *J. Sci. Industr. Res.*, vol. 17B, Feb. 1958, pp. 63-70.
Chatterjee et al., *J. Sci. Industr. Res.*, vol. 18B, Jul. 1959, pp. 272-278.
Graboyes et al., *Pteridines X.*, vol. 11 Jan. 6, 1968, pp. 568-573.
Grohe et al., *Liebigs Ann. Chem.*, 1974, pp. 2066-2073.
Gulevskaya et al., *Chemistry of Heterocyclic Compounds*, vol. 30, No. 9, 1994, pp. 1083-1091.
Hirota et al., *J. Chem. Soc. Perkin Trans. 1*, 1990, pp. 123-128.
Srivastava, et al., *Combinatorial Chemistry & High Throughout Screening*, 1999, 2, pp. 33-37.
Taylor et al., *Pyrimido [4,5-D]Pyrimidines*, vol. 82, pp. 5711-5718.
Wamhoff et al., *Heterocycles*, vol. 35, No. 2, 1993, pp. 1055-1066.
M. Hirota et al., "A Facile Synthesis of 7-Substituted Pyrimido *[4,5-d]-Pyrimidine-2,4-diones*", Synthesis, pp. 589-590 (1984).

* cited by examiner

*Primary Examiner*—Thomas C. McKenzie
(74) *Attorney, Agent, or Firm*—George W. Johnston; Patricia S. Rocha-Tramaloni

(57) ABSTRACT

Disclosed are novel pyrimido compounds that are selective inhibitors of both KDR and FGFR kinases and are selective against LCK. These compounds and their pharmaceutically acceptable salts are anti-proliferative agents useful in the treatment or control of solid tumors, in particular breast, colon, lung and prostate tumors. Also disclosed are pharmaceutical compositions containing these compounds and methods of treating cancer.

19 Claims, No Drawings

PYRIMIDO COMPOUNDS HAVING ANTIPROLIFERATIVE ACTIVITY

PRIORITY TO RELATED APPLICATIONS

This application claims the benefit of Provisional Application Ser. No. 60/423,670, filed Nov. 4, 2002.

FIELD OF THE INVENTION

The present invention is directed to novel pyrimido compounds that inhibit KDR (kinase insert domain-containing receptor) and FGFR (fibroblast growth factor receptor) kinases and are selective against LCK (T-cell tyrosine kinase $p56^{lck}$). These compounds and their pharmaceutically acceptable salts have antiproliferative activity and are useful in the treatment or control of cancer, in particular solid tumors. In addition these compounds have advantageous bioavailability profiles. This invention is also directed to pharmaceutical compositions containing such compounds and to methods of treating or controlling cancer, most particularly the treatment or control of breast, lung, colon and prostate tumors.

BACKGROUND OF THE INVENTION

Protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Tyrosine kinases are a subset of protein kinases that catalyze the transfer of the terminal phosphate of adenosine triphosphate (ATP) to tyrosine residues on protein substrates. These kinases play an important part in the propagation of growth factor signal transduction that leads to cellular proliferation, differentiation and migration.

For example, fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). See Hennequin L. F. et. al., J. Med. Chem. 2002, 45(6), pp 1300. FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. See Klohs W. E. et. al., Current Opinion in Biotechnology 1999, 10, p. 544.

There are several examples of small molecule inhibitors of protein kinase catalytic activity. In particular, small molecule inhibitors typically block the phosphorylation of substrates by tightly interacting with the protein kinase ATP binding site (or "active site"). See WO 98/24432 and Hennequin L. F. et. al., J. Med. Chem. 2002, 45(6), pp 1300. Several of these compounds inhibit multiple targets. For example, WO99/61444 (Warner-Lambert) discloses bicyclic pyrimidines and bicyclic 3,4-dihydropyrimidines of formula

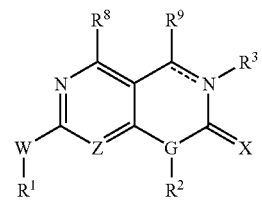

that are asserted to inhibit cyclin dependent kinases Cdk1, Cdk2 and Cdk4 as well as the growth factor receptor tyrosine kinase enzymes PDGFR and FGFR. Some compounds are also asserted to inhibit Cdk6.

U.S. Pat. No. 6,150,373 (Hoffmann-La Roche Inc.) discloses bicyclic nitrogen heterocycles of formula

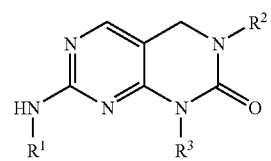

that are stated to inhibit the T-cell tyrosine kinase $p56^{lck}$.

WO 01/29041 A1 and WO 01/29042 (F. Hoffmann-La Roche A G) disclose alkylamino substituted bicyclic nitrogen heterocycles of formula

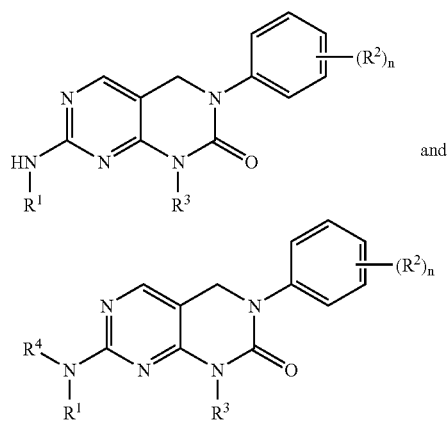

that are stated to inhibit p38 mediated cellular functions and are thus inhibitors of cellular proliferation.

WO 01/64679 A1 (SmithKline Beecham) discloses 1,5-disubstituted-3,4-dihydro-1H-pyrimido[4,5-D]pyrimidin-2-one compounds of formula

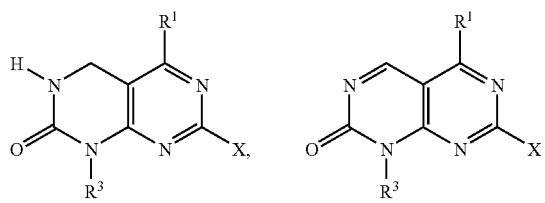

that are stated to be useful in treating CSBP/P38 kinase mediated diseases.

There continues to be a need for easily synthesized, small-molecule compounds effective in inhibiting the catalytic activity of protein kinases, in particular FGFR and KDR kinases for treating one or more types of solid tumors. It is particularly desirable to provide small molecule inhibitors that are selective for FGFR and KDR. This is desirable because of the potential concomitant toxicity and other undesirable complications that may follow from inhibiting multiple targets. It is preferable that such small molecule inhibitors also possess advantageous bioavailability profiles. It is thus an object of this invention to provide such compounds and pharmaceutical compositions containing these compounds.

SUMMARY OF THE INVENTION

The present invention relates to novel pyrimido compounds capable of selectively inhibiting the activity of KDR and FGFR. These compounds are useful in the treatment or control of cancer, in particular the treatment or control of solid tumors. In particular this invention relates to compounds of formula

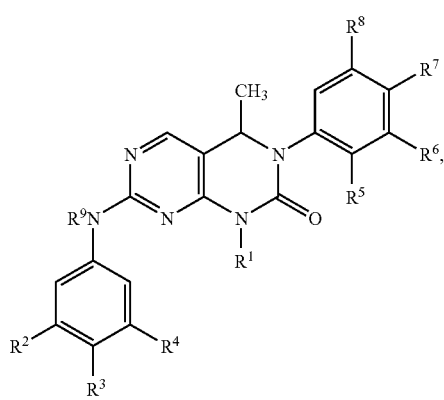

I or the pharmaceutically acceptable salts thereof, wherein $R^1$, $R^2$, $R^3$, $R^4$, $R^5$, $R^6$, $R^7$, $R^8$ and $R^9$ are as hereinafter defined.

The present invention also relates to pharmaceutical compositions comprising a therapeutically effective amount of one or more compounds of formula I and a pharmaceutically acceptable carrier or excipient.

The present invention further relates to a method for treating or controlling solid tumors, in particular treatment or control of breast, lung, colon and prostate tumors, most particularly breast or colon tumors, by administering to a human patient in need of such therapy an effective amount of a compound of formula I and/or a pharmaceutically acceptable salt thereof.

The present invention is further directed to novel intermediate compounds useful in the preparation of compounds of formula I.

DETAILED DESCRIPTION OF THE INVENTION

Definitions

As used herein, the following terms shall have the following definitions.

"Alkenyl" denotes a straight-chain or branched aliphatic hydrocarbon having at least one set of carbon-carbon double bond, for example vinyl, 2-butenyl, and 3-methyl-2-butenyl.

"Alkynyl" denotes a straight-chain or branched aliphatic hydrocarbon having at least one set of carbon-carbon triple bond, for example ethynyl, and 2-butynyl.

"Alkyl" denotes a straight-chain or branched saturated aliphatic hydrocarbon having 1 to 10, preferably 1 to 6, and more preferably 1 to 4 carbon atoms. Alkyl groups having 1 to 6 carbon atoms are also referred to herein as "lower alkyl." Typical lower alkyl groups include methyl, ethyl, propyl, isopropyl, butyl, t-butyl, 2-butyl, pentyl and hexyl. As used herein the sample designation $C_{1-4}$ alkyl means alkyl having from 1 to 4 carbon atoms.

"Alkoxy" means an alkyl radical that is attached to the remainder of the molecule by oxygen (RO—), e.g. methoxy, ethoxy.

"Aryl" means an aromatic carbocyclic radical, for example a 6–10 membered aromatic or partially aromatic ring system. Preferred aryl groups include, but are not limited to, phenyl, naphthyl, tolyl and xylyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" or "Therapeutically Effective amount" means an amount of at least one compound for formula I, or a pharmaceutically acceptable salt thereof, that significantly inhibits tumor growth.

"Halogen" means fluorine, chlorine, bromine or iodine, preferably chlorine or fluorine.

"Hetero atom" means an atom selected from N, O and S, preferably N. If the hetero atom is N, it can be present as —NH— or —N-lower alkyl-. If the hetero atom is S, it can be present as S, SO or $SO_2$.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

"Heterocycle" or "heterocyclyl" means a 3- to 10-membered saturated or partially unsaturated non-aromatic monovalent cyclic radical having from one to 3 hetero atoms selected from nitrogen, oxygen or sulfur or a combination thereof. Examples of preferred heterocycles are piperidine, piperazine, pyrrolidine, and morpholine.

"Hydroxy" is a prefix indicating the presence of a monovalent OH group.

"$IC_{50}$" refers to the concentration of a particular compound according to the invention required to inhibit 50% of a specific measured activity. $IC_{50}$ can be measured, inter alia, as is described in Example 22, infra.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

In one embodiment, the invention relates to compounds of formula

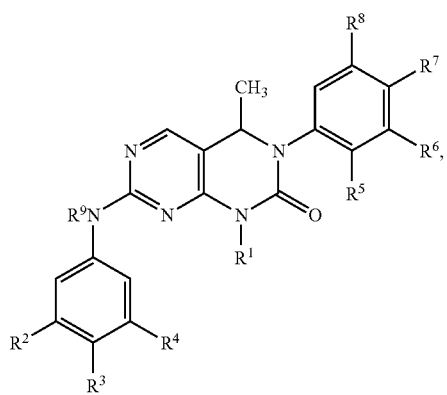

I or a pharmaceutically acceptable salt thereof, wherein
$R^1$ is selected from the group
  H,
  $C_{1-10}$ alkyl,
  $C_{1-10}$ alkyl substituted by up to three groups selected from aryl, cycloalkyl, heteroaryl, heterocycle, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$, wherein the aryl, cycloalkyl, heteroaryl, and heterocycle groups may each independently be substituted by up to three groups selected from $NR^{10}R^{11}$, $OR^{12}$, $SR^{12}$, halogen, $COR^{13}$, $CO_2R^{13}$, $CONR^{13}R^4$, $SO_2NR^{13}R^{14}$, $SOR^{13}$, $SO_2R^{13}$, CN and $NO_2$,
  aryl,
  aryl substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
  heteroaryl,
  heteroaryl substituted by up to three groups selected from lower alkyl, $NR^{10}R^{11}$, $OR^{12}$, $SR^{12}$, halogen, $COR^{13}$, $CO_2R^{13}$, $CONR^{13}R^4$, $SO_2NR^{13}R^{14}$, $SOR^{13}$, $SO_2R^{13}$, CN and $NO_2$,
  heterocycle,
  heterocycle substituted by up to three groups selected from lower alkyl, $NR^{10}R^{11}$, $OR^2$, $SR^2$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
  $C_{3-10}$ cycloalkyl,
  $C_{3-10}$ cycloalkyl substituted by up to three groups selected from lower alkyl $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
  $C_{2-10}$ alkenyl,
  $C_{2-10}$ alkenyl substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}SO_2R^{13}$ CN and $NO_2$, and
  $C_{2-10}$ alkynyl, substituted by up to three groups selected from $NR^{10}R^1$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$;
$R^2$, $R^3$ and $R^4$ are independently selected from the group consisting of
  H,
  halogen,
  $CO_2R^{13}$,
  $CONR^{13}R^{14}$
  $SO_2NR^{13}R^{14}$,
  $SO_2R^{13}$,
  CN, and
  $NO_2$;
$R^5$, $R^6$, $R^7$ and $R^8$ are independently selected from the group
  H,
  lower alkyl,
  lower alkyl substituted by hydroxy or alkoxy,
  $NR^{15}R^{16}$,
  OH,
  $OR^{17}$,
  $SR^{17}$,
  halogen,
  $COR^{17}$,
  $CO_2R^{17}$,
  $CONR^{17}R^{18}$,
  $SO_2NR^{17}R^{18}$,
  $SOR^{17}$,
  $SO_2R^{17}$, and
  CH;
$R^9$ is selected from the group
  H,

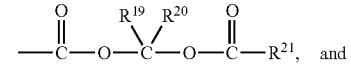

and
  $COR^{17}$;
$R^{10}$ and $R^{11}$ are independently selected from the group
  H,
  $COR^{13}$,
  $CO_2R^{13}$,
  $CONR^{13}R^{14}$,
  $SO_2R^{13}$,
  $SO_2NR^{13}R^{14}$,
  lower alkyl,
  lower alkyl substituted by hydroxy, alkoxy or $NR^{15}R^{16}$,
  cycloalkyl,
  cycloalkyl substituted by hydroxy, alkoxy, lower alkyl, or $NR^{15}R^{16}$,
  heterocycle, and
  heterocycle substituted by hydroxy, alkoxy, lower alkyl, or $NR^{15}R^{16}$, or, alternatively, NR$^{10}$R$^{11}$ can form a ring having 3 to 7 atoms, said ring optionally including one or more additional hetero atoms and being optionally substituted by the group consisting of one or more lower alkyl, OR$^{12}$, COR$^{13}$, CO$_2$R$^{13}$, CONR$^{13}$R$^{14}$, SOR$^{13}$, SO$_2$R$^{13}$, and SO$_2$NR$^{13}$R$^{14}$;

R$^{12}$ is selected from the group
H,
lower alkyl,
COR$^{13}$,
CONR$^{13}$R$^{14}$,
C$_{2-6}$ alkyl substituted by hydroxy, alkoxy, or NR$^{15}$R$^{16}$,
cycloalkyl,
cycloalkyl substituted by hydroxy, alkoxy, lower alkyl, or NR$^{15}$R$^{16}$,
heterocycle, and
heterocycle substituted by hydroxy, alkoxy, lower alkyl, or NR$^{15}$R$^{16}$, R$^{13}$ and R$^{14}$ are independently selected from the group
H,
lower alkyl,
C$_{2-6}$ alkyl substituted by hydroxy, alkoxy, or NR$^{15}$R$^{16}$,
cycloalkyl,
cycloalkyl substituted by hydroxy, alkoxy, lower alkyl, or NR$^{15}$R$^{16}$,
heterocycle, and
heterocycle substituted by hydroxy, alkoxy, lower alkyl, or NR$^{15}$R$^{16}$,
or, alternatively, NR$^{13}$R$^{14}$ can form a ring having 3 to 7 atoms, said ring optionally including one or more additional hetero atoms and being optionally substituted by the group consisting of one or more lower alkyl, OR$^{17}$, COR$^{17}$, CO$_2$R$^{17}$, CONR$^{17}$R$^{18}$, SO$_2$R$^{17}$, and SO$_2$NR$^{17}$R$^{18}$;

R$^{15}$ is selected from the group
H,
lower alkyl,
COR$^{17}$, and
CO$_2$R$^{17}$;

R$^{16}$, R$^{17}$ and R$^{1}$ are independently selected from the group
H, and
lower alkyl,
or, alternatively, NR$^{15}$R$^{16}$ and NR$^{17}$R$^{18}$ can each independently form a ring having 3 to 7 atoms, said ring optionally including one or more additional hetero atoms;

R$^{19}$ and R$^{20}$ are independently selected from the group
H, and
lower alkyl; and R$^{21}$ is selected from
lower alkyl, and
C$_{2-6}$ alkyl substituted by hydroxy, alkoxy or NR$^{15}$R$^{16}$, or the pharmaceutically acceptable salts thereof.

Compounds disclosed herein and covered by formula I above may exhibit tautomerism or structural isomerism. It is intended that the invention encompasses any tautomeric or structural isomeric form of these compounds, or mixtures of such forms (e.g. racemic mixtures), and is not limited to any one tautomeric or structural isomeric form depicted in formula I above.

When the compounds of formula I exhibit structural isomerism, the preferred optical isomer is depicted by formula Ia below In a preferred embodiment, the invention relates to a compound of formula I wherein R$^{1}$ is selected from aryl, and aryl substituted by OR$^{12}$ or CONR$^{13}$R$^{14}$.

In another preferred embodiment of the compounds of formula I, R$^{1}$ is selected from lower alkyl and C$_{2-6}$ alkyl substituted by OR$^{12}$ or CONR$^{13}$R$^{14}$.

In another preferred embodiment of the compounds of formula I, R$^{2}$ is H.

In another preferred embodiment of the compounds of formula I, R$^{2}$ and R$^{3}$ are H.

In another preferred embodiment of the compounds of formula I, R$^{2}$, R$^{3}$ and R$^{4}$ are H.

In another preferred embodiment of the compounds of formula I, R$^{3}$ is halogen, preferably F.

In another preferred embodiment of the compounds of formula I, R$^{5}$, R$^{6}$ and R$^{8}$ are H and R$^{7}$ is O-lower alkyl, preferably O—CH$_3$.

In another preferred embodiment of the compounds of formula I, R$^{5}$ is halogen, preferably F.

In another preferred embodiment of the compounds of formula I, R$^{9}$ is H.

The following compounds are preferred embodiments according to the present invention:

(±)-3-(4-Methoxy-phenyl)-4-methyl-1-phenyl-7-phenylamino-3,4-dihydro-1H-pyrimido[4,5-d]pyrimidin-2-one (Example 1g);

3-(4-Methoxy-phenyl)-4-(R)-methyl-1-phenyl-7-phenylamino-3,4-dihydro-1H-pyrimido[4,5-d]pyrimidin-2-one (Example 2);

3-(4-Methoxy-phenyl)-4-(S)-methyl-1-phenyl-7-phenylamino-3,4-dihydro-1H-pyrimido[4,5-d]pyrimidin-2-one (Example 3);

(±)-1,3-Bis-(4-methoxy-phenyl)-4-methyl-7-phenylamino-3,4-dihydro-1H-pyrimido[4,5-d]pyrimidin-2-one (Example 4b);

(±)-3-[3-(4-Methoxy-phenyl)-4-methyl-2-oxo-7-phenylamino-3,4-dihydro-2H-pyrimido[4,5-d]pyrimidin-1-yl]-benzonitrile (Example 5b);

(±)-3-[3-(4-Methoxy-phenyl)-4-methyl-2-oxo-7-phenylamino-3,4-dihydro-2H-pyrimido[4,5-d]pyrimidin-1-yl]-benzamide (Example 6);

(±)-3-(2-Fluoro-4-methoxy-phenyl)-4-methyl-1-phenyl-7-phenylamino-3,4-dihydro-1H-pyrimido[4,5-d]pyrimidin-2-one (Example 8d);

(±)-3-[3-(2-Fluoro-4-methoxy-phenyl)-4-methyl-2-oxo-7-phenylamino-3,4-dihydro-2H-pyrimido[4,5-d]pyrimidin-1-yl]-benzonitrile (Example 9b);

(±)-3-[3-(2-Fluoro-4-methoxy-phenyl)-4-methyl-2-oxo-7-phenylamino-3,4-dihydro-2H-pyrimido[4,5-d]pyrimidin-1-yl]-benzamide (Example 10);

(±)-3-(2-Chloro-5-methoxy-phenyl)-4-methyl-1-phenyl-7-phenylamino-3,4-dihydro-1H-pyrimido[4,5-d]pyrimidin-2-one (Example 12c);

1-(2-Hydroxy-1-(S)-methyl-ethyl)-3-(4-methoxy-phenyl)-4-methyl-7-phenylamino-3,4-dihydro-1H-pyrimido[4,5-d]pyrimidin-2-one (example 13d);

1-(2-Hydroxy-1-(R)-methyl-ethyl)-3-(4-methoxy-phenyl)-4-(R)-methyl-7-phenylamino-3,4-dihydro-1H-pyrimido[4,5-d]pyrimidin-2-one (Example 14f);

1-(2-Hydroxy-1-(R)-methyl-ethyl)-3-(4-methoxy-phenyl)-4-(S)-methyl-7-phenylamino-3,4-dihydro-1H-pyrimido[4,5-d]pyrimidin-2-one (Example 15b);

3-(4-Methoxy-phenyl)-4-methyl-7-phenylamino-1-[1-(S)-phenyl-ethyl]-3,4-dihydro-1H-pyrimido[4,5-d]pyrimidin-2-one (Example 18);

(±)-N-[6-(4-Methoxy-phenyl)-5-methyl-7-oxo-8-phenyl-5,6,7,8-tetrahydro-pyrimido[4,5-d]pyrimidin-2-yl]-N-phenyl-acetamide (Example 19);

(±)-1-(trans-4-Hydroxy-cyclohexyl)-3-(4-methoxy-phenyl)-4-methyl-7-phenylamino-3,4-dihydro-1H-pyrimido[4,5-d]pyrimidin-2-one (Example 20b);

1-[(1R,3R)-3-Hydroxy-cyclopentyl]-3-(4-methoxy-phenyl)-4-(S)-methyl-7-phenylamino-3,4-dihydro-1H-pyrimido[4,5-d]pyrimidin-2-one (Example 21a);

1-[(1S,3S)-3-Hydroxy-cyclopentyl]-3-(4-methoxy-phenyl)-4-(S)-methyl-7-phenylamino-3,4-dihydro-1H-pyrimido[4,5-d]pyrimidin-2-one (Example 21b);

7-(4-Fluoro-phenylamino)-1-[(1R,3R)-3-hydroxy-cyclopentyl)]-3-(4-methoxy-phenyl)-4-(S)-methyl-3,4-dihydro-1H-pyrimido[4,5-d]pyrimidin-2-one (Example 21c);

7-(4-Fluoro-phenylamino)-1-[(1S,3S)-3-hydroxy-cyclopentyl)]-3-(4-methoxy-phenyl)-4-(S)-methyl-3,4-dihydro-1H-pyrimido[4,5-d]pyrimidin-2-one (Example 21d);

7-(4-Fluoro-phenylamino)-1-(2-hydroxy-1-(R)-methyl-ethyl)-3-(4-methoxy-phenyl)-4-(S)-methyl-3,4-dihydro-1H-pyrimido[4,5-d]pyrimidin-2-one (Example 21e);

3-(4-Chloro-phenyl)-7-(4-fluoro-phenylamino)-1-(2-hydroxy-1-(R)-methyl-ethyl)-4-(S)-methyl-3,4-dihydro-1H-pyrimido[4,5-d]pyrimidin-2-one (Example 21f);

3-(4-Chloro-2-fluoro-phenyl)-7-(4-fluoro-phenylamino)-1-(2-hydroxy-1-(R)-methyl-ethyl)-4-(S)-methyl-3,4-dihydro-1H-pyrimido[4,5-d]pyrimidin-2-one (Example 21g);

3-(4-Chloro-phenyl)-1-(2-hydroxy-1-(R)-methyl-ethyl)-4-(S)-methyl-7-phenylamino-3,4-dihydro-1H-pyrimido[4,5-d]pyrimidin-2-one (Example 21h);

3-(4-Chloro-2-fluoro-phenyl)-1-(2-hydroxy-1-(R)-methyl-ethyl)-4-(S)-methyl-7-phenylamino-3,4-dihydro-1H-pyrimido[4,5-d]pyrimidin-2-one (Example 21i);

3-(4-Chloro-phenyl)-1-(3-hydroxy-2-(S)-methyl-propyl)-4-(S)-methyl-7-phenylamino-3,4-dihydro-1H-pyrimido[4,5-d]pyrimidin-2-one (Example 21j); and 3-(4-Chloro-2-fluoro-phenyl)-1-(3-hydroxy-2-(S)-methyl-propyl)-4-(S)-methyl-7-phenylamino-3,4-dihydro-1H-pyrimido[4,5-d]pyrimidin-2-one (Example 21k).

The compounds of the invention are selective for FGF and KDR kinases. These compounds are useful in the treatment or control of cancer, in particular the treatment or control of solid tumors, specifically breast, lung, colon and prostate tumors. These compounds are highly permeable to cell membranes and thus possess advantageous bioavailability profiles such as improved oral bioavailability.

General Synthesis of Compounds According to the Invention

The compounds of the present invention can be prepared by any conventional means. Suitable processes for synthesizing these compounds are provided in the examples. Generally, compounds of formula I can be prepared according to the below described synthetic routes.

Scheme 1

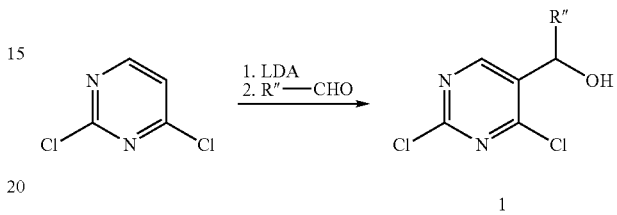

Scheme 2

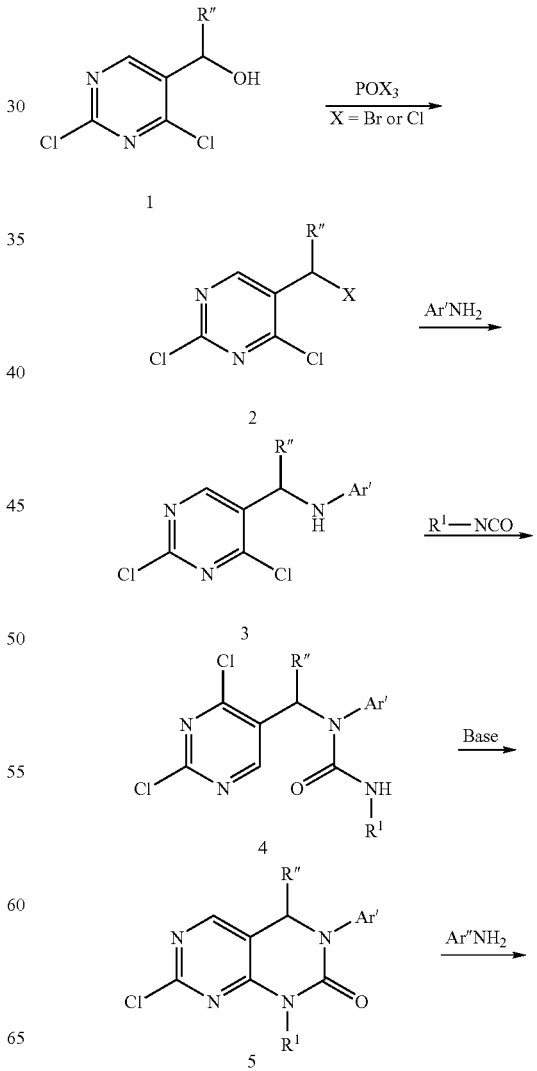

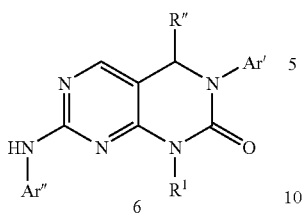

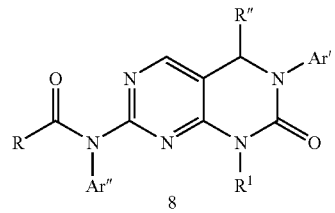

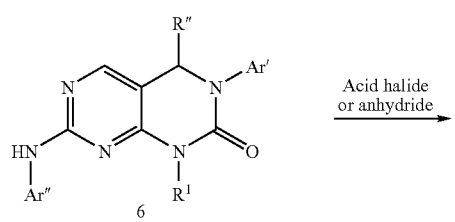

Compositions/Formulations

In an alternative embodiment, the present invention relates to pharmaceutical compositions comprising at least one compound of formula I, or a pharmaceutically acceptable salt or ester thereof.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, stearic acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, in particular oncological disorders. These compounds and formulations containing said compounds are particularly useful in the treatment or control of solid tumors, such as, for example, breast, colon, lung and prostate tumors. Thus, the present invention is further directed to a method for treating such solid tumors by administering to a patient in need of such therapy an effective amount of a compound of formula I and/or its salt.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention is also directed to the following novel intermediates useful in the synthesis of compounds of formula I:

(±)-[1-(2,4-Dichloro-pyrimidin-5-yl)-ethyl]-(4-methoxy-phenyl)-amine (Example 1d);

(±)-7-Chloro-3-(4-methoxy-phenyl)-4-methyl-1-phenyl-3,4-dihydro-1H-pyrimido[4,5-d]pyrimidin-2-one (Example 1e);

(±)-{2-Chloro-5-[1-(4-methoxy-phenylamino)-ethyl]-pyrimidin-4-yl}-(4-methoxy-phenyl)-amine (Example 1f);

(±)-7-Chloro-1,3-bis-(4-methoxy-phenyl)-4-methyl-3,4-dihydro-1H-pyrimido[4,5-d]pyrimidin-2-one (Example 4a);

(±)-3-[7-Chloro-3-(4-methoxy-phenyl)-4-methyl-2-oxo-3,4-dihydro-2H-pyrimido[4,5-d]pyrimidin-1-yl]-benzonitrile (Example 5a);

(±)-[1-(2,4-Dichloro-pyrimidin-5-yl)-ethyl]-(2-fluoro-4-methoxy-phenyl)-amine (Example 8b);

(±)-7-Chloro-3-(2-fluoro-4-methoxy-phenyl)-4-methyl-1-phenyl-3,4-dihydro-1H-pyrimido[4,5-d]pyrimidin-2-one (Example 8c);

(±)-3-[7-Chloro-3-(2-fluoro-4-methoxy-phenyl)-4-methyl-2-oxo-3,4-dihydro-2H-pyrimido[4,5-d]pyrimidin-1-yl]-benzonitrile (Example 9a);

(±)-(2-Chloro-5-methoxy-phenyl)-[1-(2,4-dichloro-pyrimidin-5-yl)-ethyl]-amine (Example 12a);

(±)-7-Chloro-3-(2-chloro-5-methoxy-phenyl)-4-methyl-1-phenyl-3,4-dihydro-1H-pyrimido[4,5-d]pyrimidin-2-one (Example 12b);

1-[2-(tert-Butyl-diphenyl-silanyloxy)-1-(S)-methyl-ethyl]-7-chloro-3-(4-methoxy-phenyl)-4-methyl-3,4-dihydro-1H-pyrimido[4,5-d]pyrimidin-2-one (Example 13c);

3-[2-tert-Butyl-diphenyl-silanyloxy-1-(R)-methyl-ethyl]-1-(R)-[1-(2,4-dichloropyrimidin-5-yl)-ethyl]-1-(4-methoxyphenyl)-urea (Example 14c);

3-[2-tert-Butyl-diphenyl-silanyloxy-1-(R)-methyl-ethyl]-1-(S)-[1-(2,4-dichloropyrimidin-5-yl)-ethyl]-1-(4-methoxyphenyl)-urea (Example 14d);

1-[2-(tert-Butyl-diphenyl-silanyloxy)-1-(R)-methyl-ethyl]-7-chloro-3-(4-methoxy-phenyl)-(R)-4-methyl-3,4-dihydro-1H-pyrimido[4,5-d]pyrimidin-2-one (Example 14e);

1-[2-(tert-Butyl-diphenyl-silanyloxy)-1-(R)-methyl-ethyl]-7-chloro-3-(4-methoxy-phenyl)-4-(S)-methyl-3,4-dihydro-1H-pyrimido[4,5-d]pyrimidin-2-one (Example 15a);

1-[1-(2,4-Dichloro-pyrimidin-5-yl)-ethyl]-1-(4-methoxy-phenyl)-3-[1-(S)-phenyl-ethyl]-urea (Example 16); and 7-Chloro-3-(4-methoxy-phenyl)-4-methyl-1-[1-(S)-phenyl-ethyl]-3,4-dihydro-1H-pyrimido[4,5-d]pyrimidin-2-one (Example 17).

EXAMPLES

The following examples illustrate preferred methods for synthesizing the compounds and formulations of the present invention.

Example 1

Example 1a (±)-1-(2,4-Dichloro-pyrimidin-5-yl)-ethanol

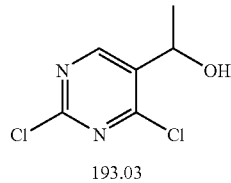

193.03

(±)-1-(2,4-Dichloro-pyrimidin-5-yl)-ethanol was synthesized from 2,4-dichloropyrimidine (Aldrich) according to the literature procedure of Pie, N.; Turck, A.; Martin, P.; Barbey, S.; Queguiner, G. *Tet. Lett,* 1993 (34), 1605–1608.

Example 1b (±)-2,4-Dichloro-5-(1-chloroethyl)-pyrimidine

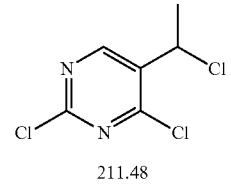

211.48

To a solution of (±)-1-(2,4-dichloro-pyrimidin-5-yl)-ethanol (1.27 g, 6.60 mmol) (from Example 1a supra) in phosphorus oxychloride (5.0 mL, 53.11 mmol) (Aldrich), at 0° C., was added diisopropylethyl-amine (2.60 mL, 14.78 mmol) (Aldrich). The reaction was stirred at 0° C. for 5 minutes, at ambient temperature for 15 minutes and then at 115° C. for 3 hours. The reaction was cooled to room temperature, diluted with toluene (10 mL) and the mixture was then poured into ice (15 g). After stirring for 10 minutes, the layers were separated and the aqueous extract was back washed with toluene. The combined organic extracts were dried over anhydrous sodium sulfate, filtered, and concentrated. Purification by flash chromatography (Biotage, 40M, 10:90 to 15:85 ethyl acetate-hexanes gradient) gave (±)-2,4-dichloro-5-(1-chloroethyl)-pyrimidine as an oil. (Yield 1.233 g; 88.3%).

Example 1c (±)-2,4-Dichloro-5-(1-bromoethyl)-pyrimidine

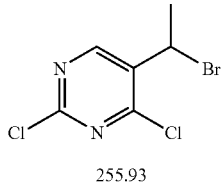

255.93

A solution of (±)-1-(2,4-dichloro-pyrimidin-5-yl)-ethanol (0.50 g; 2.60 mmol) (from Example 1a supra) and diisopropylethylamine (1.10 mL; 6.25 mmol) (Aldrich) in dibromomethane (0.35 mL) was cooled to 15° C. Phosphorus oxybromide (0.73 g; 2.83 mmol) was added in one portion. Cooling bath was removed and reaction mixture was stirred at room temperature. After 20 minutes, the reaction was diluted with ethyl acetate and water. The organic phase was washed with brine and then dried over anhydrous sodium sulfate, filtered and concentrated to give crude (±)-2,4-dichloro-5-(1-bromoethyl)-pyrimidine (0.61 g; 91.4%). Purification by flash chromatography (Biotage, 40M, 10:90 ethyl acetate-hexanes) gave pure (±)-2,4-dichloro-5-(1-bromoethyl)-pyrimidine as an oil which solidified when stored in refrigerator.

Alternatively (±)-2,4-dichloro-5-(1-bromoethyl)-pyrimidine was prepared as follows.

Ethyl 2-formylbutyrate

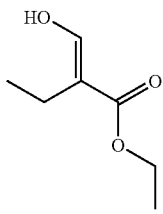

A solution of diisopropylamine (120.6 mL, 0.86 mol) (Aldrich) in tetrahyrofuran (370 mL) was cooled to –30° C. n-Butyllithium (2.5 M in hexanes, 344.2 mL, 0.86 mol) (Aldrich) was added dropwise at such a rate that the reaction mixture temperature was kept between –30 to 0° C. The reaction mixture was then cooled to –75° C. in a dry ice-acetone bath. A solution of ethyl butyrate (100 g, 0.86 mol) (Aldrich) in tetrahydrofuran (170 mL) was added dropwise over 28 minutes and keeping the reaction temperature between –75 to –70° C. The mixture was stirred at the same temperature for an additional 30 minutes. Ethyl formate (125 mL, 1.55 mol) (Aldrich) was then added to this mixture over 25 minutes and maintaining the temperature between –75 to –70° C. The resultant mixture was allowed to warm to room temperature and stirred at room temperature for 3 hours. With external cooling in a cold water bath to keep the reaction temperature below 30° C. acetic acid (98.55 mL, 1.72 mol) was added, followed by water (430 mL) and dichloromethane (200 mL). After separating the layers, the organic layer was washed with water (300 mL). The combined water layer was extracted with dichloromethane (200 mL). The combined organic layer was washed with aqueous sodium bicarbonate solution (200 mL). The basic aqueous solution was extracted with dichloromethane (100 mL). All organic layers were then combined, dried over sodium sulfate over night, filtered and distilled to remove solvent leaving about 180 mL. (Some of the product was distilled over with tetrahydrofuran.) The residue was distilled at 65–81° C. (23 mm Hg). The fraction distilling over at 70–81° C. (23 mm Hg) gave ethyl 2-formylbutyrate. (Yield 68.35 g, 55.1%).

5-Ethyl Uracil

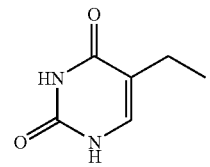

Urea (19.39 g, 0.32 mol) (J. T. Baker) was added over 20 minutes to fuming sulfuric acid (26–29.5% free $SO_3$, 135 mL, 2.65 mol) (Aldrich) with cooling in an ice water bath maintaining the reaction temperature between 8 to 15° C. After stirring for an additional 30 minutes, ethyl 2-formylbutyrate (46.55 g, 0.32 mol) (from Example 1c, supra) was added over 18 minutes keeping the reaction at the same temperature. After stirring for another 30 minutes, a second portion of urea (15.07 g, 0.25 mol) was added over 10 minutes at the same temperature. The reaction mixture was then stirred at room temperature for 65 hours, and at 90–100° C. for 2 hours (gas evolution was observed, and reaction was exothermic, with reaction temperature rising to 110° C.). The mixture was cooled to 30° C. with an ice-water bath. Ice (270 g) was added slowly keeping the reaction below 35° C. The mixture was then cooled to 5° C. and stirred for 20 minutes. The solid formed was collected by filtration, washed with cold water, hexanes, and diethyl ether and dried by suction to give 5-ethyl uracil. (Yield 38.85 g, 85.9%).

2,4-Dichloro-5-ethylpyrimidine

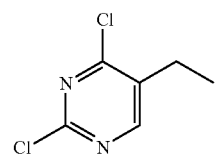

N,N-Diisopropylethylamine (195 mL, 0.86 mol) (Aldrich) was added slowly to a mixture of 5-ethyl uracil (52.3 g, 0.37 mol) (from Example 1c, supra) and phosphorous oxychloride (150 mL, 1.61 mol) (Aldrich) with external cooling in a cold water bath. The mixture was heated at reflux for 3.8 hours and cooled to room temperature. Mixture was then poured into ice (300 g). Ethyl acetate (100 mL) was added and mixture stirred at 20° C. for 30 minutes with cooling in an ice-water bath. The resulting mixture was filtered through Celite® and the filtrate extracted with ethyl acetate-hexanes (1:1, 3300 mL). The combined organic layers was washed with water (250 mL), dried over sodium sulfate, filtered and concentrated to dryness. This residue was dissolved in ethyl acetate-hexanes 1:1) and filtered through TLC grade silica gel and eluting with the same solvent. The filtrate was concentrated to dryness to give 2,4-dichloro-5-ethyl-pyrimidine. (Yield 56.3 g, 85.2%).

(±)-2,4-Dichloro-5-(1-bromoethyl)-pyrimidine

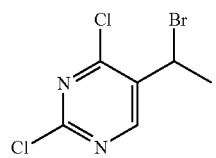

N-Bromosuccimimide (64.2 g, 0.35 mol) (Aldrich) and 2,2'-azo-bis-isobutyronitrile (AIBN, 1.78 g) (Aldrich) were added to a solution of 2,4-dichloro-5-ethylpyrimidine (56.3 g, 0.32 mol) (from Example 1c, supra) in carbon tetrachloride (400 mL). The mixture was heated at reflux for 1.5 hours and cooled to room temperature. Reaction mixture was filtered through TLC grade silica gel and eluted with ethyl acetate-hexanes (1:8). The filtrate was concentrated to dryness to give (±)-2,4-dichloro-5-(1-bromoethyl)-pyrimidine. (Yield 81.3 g, 100%).

Example 1d (±)-[1-(2,4-Dichloro-pyrimidin-5-yl)-ethyl]-(4-methoxy-phenyl)-amine

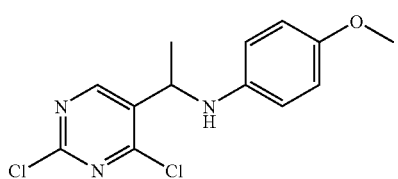

298.17

(±)-2,4-Dichloro-5-(1-bromoethyl)-pyrimidine (1.97 g; 7.70 mmol) (from Example 1c supra) was dissolved in acetonitrile (21 mL). p-Anisidine (0.95 g; 7.70 mmol) (Aldrich), potassium carbonate (1.17 g; 8.48 mmol) and potassium iodide (0.32 g; 1.93 mmol) were added and the mixture was stirred at room temperature. After 16 hours, the mixture was partitioned between ethyl acetate and water. The organic phase was washed with water and brine, dried over anhydrous sodium sulfate, filtered and concentrated. Purification by flash chromatography (Biotage 40M, 20:80 to 25:75 ethyl acetate-hexanes gradient) gave (±)-[1-(2,4-dichloro-pyrimidin-5-yl)-ethyl]-(4-methoxy-phenyl)-amine. (Yield 1.82 g; 76.3%).

Example 1e (±)-7-Chloro-3-(4-methoxy-phenyl)-4-methyl-1-phenyl-3,4-dihydro-1H-pyrimido[4,5-d]pyrimidin-2-one

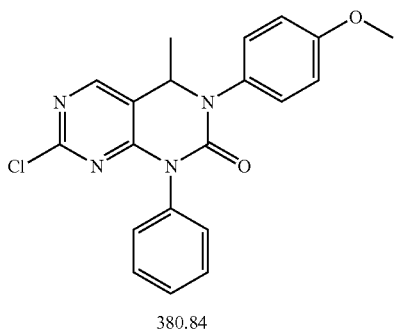

380.84

To a solution of (±)-[1-(2,4-dichloro-pyrimidin-5-yl)-ethyl]-(4-methoxy-phenyl)-amine (0.14 g; 0.46 mmol) (from Example 1c supra) in toluene (1 mL) was added phenyl isocyanate (50 µL; 0.46 mmol) (Aldrich). The solution was heated in an oil bath at 110° C. After 1 hour, a small amount of starting pyrimidine remained. An additional portion of phenyl isocyanate (7.5 µL; 0.07 mmol) was added and the mixture heated for an additional 15 minutes. Upon cooling to room temperature, the reaction was concentrated. The residue was triturated with hexanes and then dried briefly under high vacuum.

This solid residue (intermediate urea) was dissolved in freshly distilled tetrahydrofuran (1 mL), cooled to −3° C. and treated with potassium tert-butoxide (1.0 M in tetrahydrofuran; 0.5 mL; 0.5 mmol) (Aldrich). After 15 minutes in the cold, the reaction mixture was filtered through a silica gel pad (2.9 g silica) and washed with 1:1 ethyl acetate-hexanes and then ethyl acetate. The filtrates were combined and concentrated. Purification by flash chromatography (Biotage, 40S, 35:65 to 50:50 ethyl acetate-hexanes gradient) gave (±)-7-chloro-3-(4-methoxy-phenyl)-4-methyl-1-phenyl-3,4-dihydro-1H-pyrimido[4,5-d]pyrimidin-2-one as a solid. (Yield 0.14 g; 77.7%).

Example 1f (±)-{2-Chloro-5-[1-(4-methoxy-phenylamino)-ethyl]-pyrimidin-4-yl}-(4-methoxy-phenyl)-amine

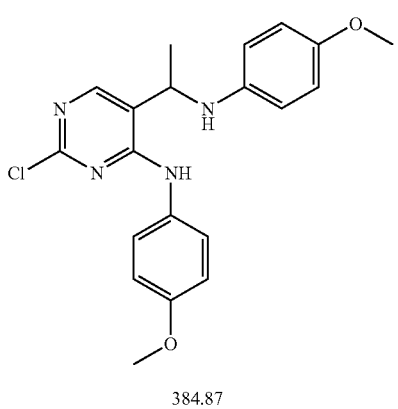

384.87

(±)-2,4-Dichloro-5-(1-chloroethyl)-pyrimidine (0.41 g; 1.94 mmol) (from Example 1b supra) was dissolved in acetonitrile (2 mL). p-Anisidine (0.25 g; 2.03 mmol) (Aldrich), potassium carbonate (0.30 g; 2.19 mmol) and potassium iodide (0.04 g; 0.23 mmol) were added and the mixture was stirred at room temperature. After 40 hours, the mixture was partitioned between ethyl acetate and water. The organic phase was washed with water and brine, dried over anhydrous sodium sulfate, filtered and concentrated. Purification by flash chromatography (Biotage 40M, 20:80 to 50:50 ethyl acetate-hexanes gradient) gave (i)-{2-chloro-5-[1-(4-methoxy-phenylamino)-ethyl]-pyrimidin-4-yl}-(4-methoxy-phenyl)-amine. (Yield 0.19 g; 25.9%).

Example 1g (±)-3-(4-Methoxy-phenyl)-4-methyl-1-phenyl-7-phenylamino-3,4-dihydro-1H-pyrimido[4,5-d]pyrimidin-2-one

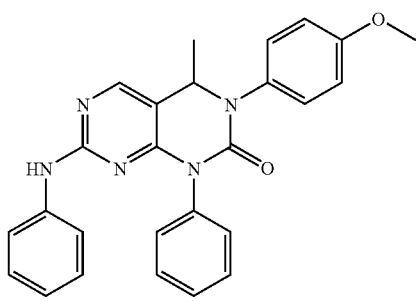

437.51

(±)-7-Chloro-3-(4-methoxy-phenyl)-4-methyl-1-phenyl-3,4-dihydro-1H-pyrimido[4,5-d]pyrimidin-2-one (0.13 g; 0.33 mmol) (from Example 1e supra) was combined with aniline (100 μL; 1.10 mmol) (Aldrich). The mixture was heated to 110° C. A clear solution resulted upon heating and then a new solid precipitated out of solution. Reaction mixture was cooled to room temperature after 45 minutes. The residue was triturated with hexanes and then purified by flash chromatography (Biotage, 40M, 40:60 to 50:50 ethyl acetate-hexanes gradient) to give (±)-3-(4-methoxy-phenyl)-4-methyl-1-phenyl-7-phenylamino-3,4-dihydro-1H-pyrimido[4,5-d]pyrimidin-2-one as an off-white solid, after crystallization from ethyl acetate-hexanes. (Yield 21.6 mg; 14.8%). A substantial amount of (±)-3-(4-methoxy-phenyl)-4-methyl-1-phenyl-7-phenylamino-3,4-dihydro-1H-pyrimido[4,5-d]pyrimidin-2-one adhered to the silica and was eluted with 50:50 ethyl acetate-methanol. (Yield 88 mg; 60%). Melting Point: 222–234° C.

HR-MS(ES$^+$) m/z Calculated for $C_{26}H_{23}N_5O_2$ [(M+H)$^+$]: 438.1925. Found: 438.1927.

Example 2

3-(4-Methoxy-phenyl)-4-(R)-methyl-1-phenyl-7-phenylamino-3,4-dihydro-1H-pyrimido[4,5-d]pyrimidin-2-one

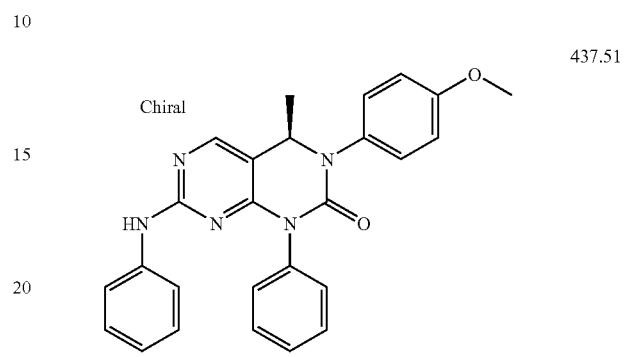

437.51

The racemic (±)-3-(4-methoxy-phenyl)-4-methyl-1-phenyl-7-phenylamino-3,4-dihydro-1H-pyrimido[4,5-d]pyrimidin-2-one (from Example 1g supra) was resolved on a Chiracel OD column (1.025 cm) in multiple runs. The first eluting peak gave 3-(4-methoxy-phenyl)-4-(R)-methyl-1-phenyl-7-phenylamino-3,4-dihydro-1H-pyrimido[4,5-d]pyrimidin-2-one. Melting Point: 218–233° C.

Example 3

3-(4-Methoxy-phenyl)-4-(S)-methyl-1-phenyl-7-phenylamino-3,4-dihydro-1H-pyrimido[4,5-d]pyrimidin-2-one

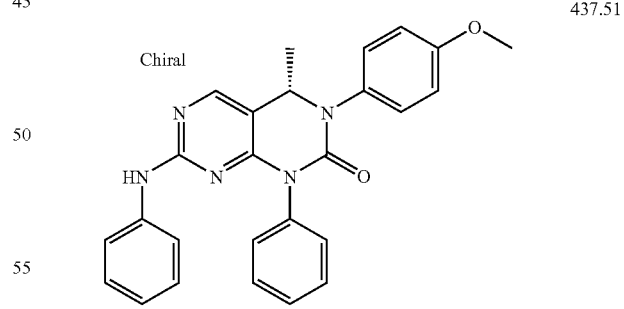

437.51

The racemic (±)-3-(4-methoxy-phenyl)-4-methyl-1-phenyl-7-phenylamino-3,4-dihydro-1H-pyrimido[4,5-d]pyrimidin-2-one (from Example 1g supra) was resolved on a Chiracel OD column (1.025 cm) in multiple runs. The second eluting peak gave 3-(4-methoxy-phenyl)-4-(S)-methyl-1-phenyl-7-phenylamino-3,4-dihydro-1H-pyrimido[4,5-d]pyrimidin-2-one. Melting Point: 223–236° C.

Example 4a (±)-7-Chloro-1,3-bis-(4-methoxy-phenyl)-4-methyl-3,4-dihydro-1H-pyrimido[4,5-d]pyrimidin-2-one

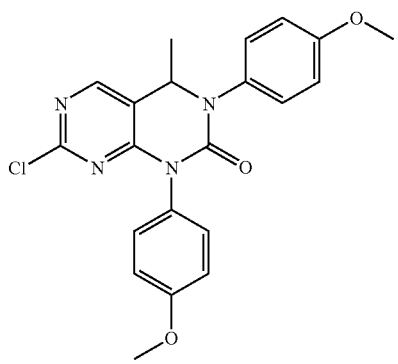

410.86

A solution of (±)-{2-chloro-5-[1-(4-methoxy-phenylamino)-ethyl]-pyrimidin-4-yl}-(4-methoxy-phenyl)-amine (49.4 mg; 0.13 mmol) (from Example 1f supra) in dichloromethane (1.5 mL) was cooled in an ice-water bath. To this solution was added triethylamine (0.18 mL; 1.29 mmol) (Aldrich), followed by phosgene solution (1.89 M, 0.34 mL; 0.64 mmol) (Fluka). After two hours in the cold, the reaction was diluted with additional dichloromethane and washed sequentially with water, dilute aqueous hydrochloric acid, dilute aqueous sodium bicarbonate, and brine. The organic layer was then dried over anhydrous sodium sulfate and concentrated. Residue was purified by flash chromatography (Biotage, 12M, 40:60 ethyl acetate-hexanes as solvent) to give (±)-7-chloro-1,3-bis-(4-methoxy-phenyl)-4-methyl-3,4-dihydro-1H-pyrimido[4,5-d]pyrimidin-2-one as a white solid. (Yield 42.6 mg; 79.2%).

Example 4b (±)-1,3-Bis-(4-methoxy-phenyl)-4-methyl-7-phenylamino-3,4-dihydro-1H-pyrimido[4,5-d]pyrimidin-2-one

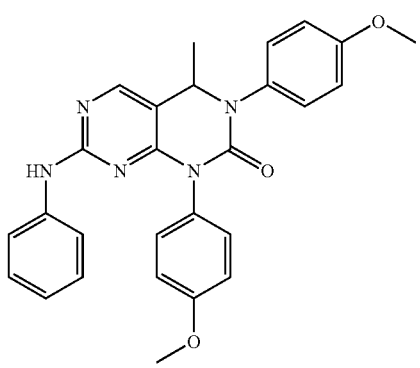

467.53

The mixture of (±)-7-chloro-1,3-bis-(4-methoxy-phenyl)-4-methyl-3,4-dihydro-1H-pyrimido[4,5-d]pyrimidin-2-one (0.30 g; 0.72 mmol) (from Example 4a supra) and aniline (0.20 mL; 2.16 mmol) (Aldrich) was heated at 100° C. for 40 minutes. The mixture was then cooled to room temperature and triturated with hexanes. The resulting solid was dissolved in dichloromethane, washed with water and brine, dried over sodium sulfate and concentrated. The residue was purified by flash chromatography (Biotage, 12S, dichloromethane followed by 30:70 to 50:50 ethyl acetate-hexanes gradient) to give (±)-1,3-bis-(4-methoxy-phenyl)-4-methyl-7-phenylamino-3,4-dihydro-1H-pyrimido[4,5-d]pyrimidin-2-one. (Yield 0.303 g; 90.1%).

The material purified by chromatography was combined with comparable material from another experiment. The combined lot was recrystallized from dichloromethane-ethyl acetate-hexanes to yield (±)-1,3-bis-(4-methoxy-phenyl)-4-methyl-7-phenylamino-3,4-dihydro-1H-pyrimido[4,5-d]pyrimidin-2-one as an off-white solid. (Yield 0.39 g; 91%). Melting Point: 228–234° C.

HR-MS(ES+) m/z Calculated for $C_{27}H_{25}N_5O_3$ [(M+H)+]: 468.2030. Found: 468.2032.

Example 5a (±)-3-[7-Chloro-3-(4-methoxy-phenyl)-4-methyl-2-oxo-3,4-dihydro-2H-pyrimido[4,5-d]pyrimidin-1-yl]-benzonitrile

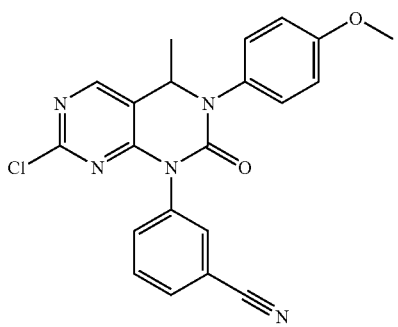

405.85

To a solution of (±)-[1-(2,4-dichloro-pyrimidin-5-yl)-ethyl]-(4-methoxy-phenyl)-amine (0.10 g; 0.34 mmol) (from Example 1d supra) in toluene (1 mL) was added 3-cyanophenyl isocyanate (66.6 mg; 0.46 mmol) (Aldrich). The mixture was heated in an oil bath at 110° C. for two hours. After cooling to room temperature, the reaction was concentrated under reduced pressure. The residue was triturated with hexanes and dried briefly. The solid residue (intermediate urea) was taken up in freshly distilled tetrahydrofuran (1.5 mL), cooled in an ice-brine bath and treated with potassium tert-butoxide (1.0 M in tetrahydrofuran; 370 µL; 0.37 mmol) (Aldrich). After 15 minutes in the cold the reaction was complete by TLC analysis and was filtered through a silica gel pad (0.5 g) and washed with ethyl acetate. The filtrate was concentrated and the residue was purified by flash chromatography (Biotage, 12M, 40:60 ethyl acetate-hexanes) to give (±)-3-[7-chloro-3-(4-methoxy-phenyl)-4-methyl-2-oxo-3,4-dihydro-2H-pyrimido[4,5-d]pyrimidin-1-yl]-benzonitrile as a solid. (Yield 0.13 g; 85.6%).

Example 5b (±)-3-[3-(4-Methoxy-phenyl)-4-methyl-2-oxo-7-phenylamino-3,4-dihydro-2H-pyrimido[4,5-d]pyrimidin-1-yl]-benzonitrile

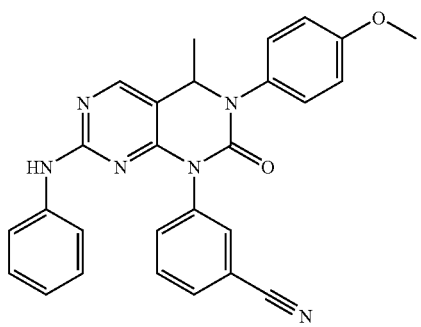

A mixture of (±)-3-[7-chloro-3-(4-methoxy-phenyl)-4-methyl-2-oxo-3,4-dihydro-2H-pyrimido[4,5-d]pyrimidin-1-yl]-benzonitrile (0.49 g; 1.21 mmol) (from Example 5a supra) and aniline (0.50 mL; 5.49 mmol) (Aldrich) was heated to 110° C. for one hour. Methanol was added to the hot mixture and the solution was then cooled. The solid that precipitated out of solution was collected and recrystallized from methanol to yield (±)-3-[3-(4-methoxy-phenyl)-4-methyl-2-oxo-7-phenylamino-3,4-dihydro-2H-pyrimido[4,5-d]pyrimidin-1-yl]-benzonitrile as a white solid. (Yield 0.35 g; 62.2%). Melting Point: 224–228° C.

HR-MS(ES$^+$) m/z Calculated for $C_{27}H_{22}N_6O_2$ ([M+H]$^+$): 463.1877; Found: 463.1883.

Example 6

(±)-3-[3-(4-Methoxy-phenyl)-4-methyl-2-oxo-7-phenylamino-3,4-dihydro-2H-pyrimido[4,5-d]pyrimidin-1-yl]-benzamide

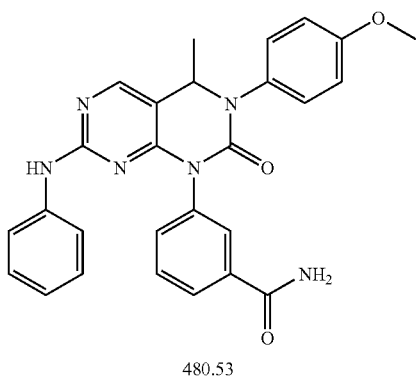

480.53

A solution of (±)-3-[3-(4-methoxy-phenyl)-4-methyl-2-oxo-7-phenylamino-3,4-dihydro-2H-pyrimido[4,5-d]pyrimidin-1-yl]-benzonitrile (0.11 g; 0.22 mmol) (from Example 5b supra) in dimethyl sulfoxide (1.5 mL) was cooled in an ice-water bath. Aqueous sodium hydroxide (1.0 M; 0.38 mL; 0.38 mmol) was added, followed by aqueous hydrogen peroxide (30% solution; 70 μL; 0.69 mmol). The cooling bath was removed following the additions and the mixture was stirred at room temperature for 3 hours. The solid was collected and washed with water and hot dichloromethane. This crude material was purified by flash chromatography (Biotage; 12M; 99:1 to 80:20 ethyl acetate-methanol gradient) and the pure product crystallized out of solution upon concentration to give (±)-3-[3-(4-methoxy-phenyl)-4-methyl-2-oxo-7-phenylamino-3,4-dihydro-2H-pyrimido[4,5-d]pyrimidin-1-yl]-benzamide as a white solid. (Yield 64.6 mg; 57.9%). Melting Point: 268–273° C. (discolored on melting).

HR-MS(EI) m/z Calculated for $C_{27}H_{24}N_6O_3$ [M$^+$]: 480.1910; Found: 480.1912.

Example 7a (±)-1-(2,4-Dichloro-pyrimidin-5-yl)-propan-1-ol

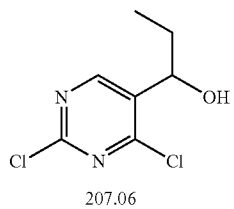

207.06

Diisopropylamine (1.10 mL; 7.85 mmol) (Aldrich) was dissolved in freshly distilled tetrahydrofuran (15 mL) and cooled to −78° C. n-Butyllithium (2.5 M in hexanes, 3.10 mL; 7.75 mmol) (Aldrich) was added dropwise and stirring continued for 30 minutes to give a LDA solution. A solution of 2,4-dichloropyrimidine (0.50 g; 3.36 mmol) (Aldrich) in tetrahydrofuran (3 mL) was added to this freshly prepared LDA solution over 12 minutes. After 30 minutes stirring at −78° C., propionaldehyde (0.48 mL; 6.65 mmol) (Aldrich) was added over 6 minutes and stirring continued for another 35 minutes. The reaction was quenched with the addition of 25% aqueous ammonium chloride solution (15 mL) and was then diluted with ethyl acetate and water. The organic phase was washed with a second portion of ammonium chloride solution and then brine, dried over anhydrous sodium sulfate and concentrated. The residue was purified by flash chromatography (Biotage; 40M; 15:85 to 25:75 ethyl acetate-hexanes gradient) to give (±)-1-(2,4-dichloro-pyrimidin-5-yl)-propan-1-ol. (Yield 0.260 g; 37%).

Example 7b (±)-5-(1-Bromopropyl)-2,4-dichloro-pyrimidine

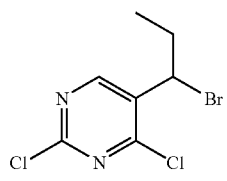

269.96

A solution of (±)-1-(2,4-dichloro-pyrimidin-5-yl)-propan-1-ol (0.26 g; 1.26 mmol) (from Example 7a supra) in diisopropylethylamine (0.55 mL; 3.13 mmol) (Aldrich) was cooled slightly (18° C.) to help offset the exothermicity of the reaction. Neat phosphorus oxybromide (0.35 g; 1.36 mmol) (Aldrich) was added in one portion. The cooling bath was removed and reaction mixture stirred at room temperature. After 15 minutes, the reaction mixture was diluted with ice and ethyl acetate. The organic phase was then washed with brine, dried over anhydrous sodium sulfate, filtered and concentrated. Purification by flash chromatography (Biotage 12M; 5:95 ethyl acetate-hexanes) gave crude (±)-5-(1-bromopropyl)-2,4-dichloro-pyrimidine which was used in subsequent steps without further purification. (Yield 0.23 g). The material showed 3 peaks for the pyrimidine ring proton in its NMR spectrum indicating some displacement of the ring chlorines with bromine.

Example 7c (±)-[1-(2,4-Dichloro-pyrimidin-5-yl)-propyl]-(4-methoxy-phenyl)-amine

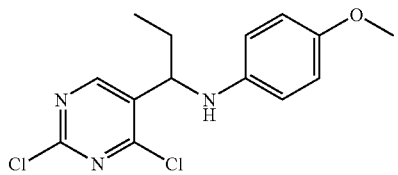

312.20

(±)-5-(1-Bromopropyl)-2,4-dichloro-pyrimidine (0.26 g; 0.96 mmol) (from Example 7b supra) was dissolved in acetonitrile (2.5 mL). p-Anisidine (0.12 g; 0.96 mmol) (Aldrich), potassium carbonate (0.15 g; 1.05 mmol) and potassium iodide (0.04 g; 0.24 mmol) were added and the mixture was stirred at room temperature. After 16 hours, the mixture was partitioned between ethyl acetate and water. The organic phase was washed with water and brine, dried over anhydrous sodium sulfate, filtered and concentrated. Purification by flash chromatography (Biotage 40S, 15:85 to 20:80 ethyl acetate-hexanes gradient) gave crude (±)-[1-(2, 4-dichloro-pyrimidin-5-yl)-propyl]-(4-methoxy-phenyl)-amine. (Yield 0.19 g; 64.3%). This material again showed 3 peaks for the pyrimidine ring proton in the same ratio as was seen in the starting material. This material was used without further purification.

Example 7d (±)-7-Chloro-4-ethyl-3-(4-methoxy-phenyl)-1-phenyl-3,4-dihydro-1H-pyrimido[4,5-d]pyrimidin-2-one

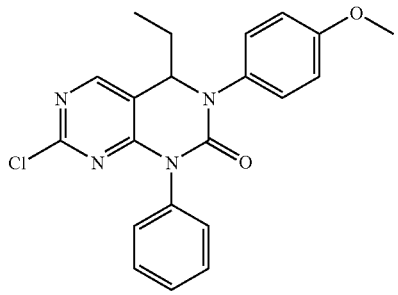

394.86

To a solution of (±)-[1-(2,4-dichloro-pyrimidin-5-yl)-propyl]-(4-methoxy-phenyl)-amine (0.19 g; 0.59 mmol) (from Example 7c supra) in toluene (2 mL) was added phenyl isocyanate (83 μL; 0.76 mmol) (Aldrich). The solution was heated in an oil bath at 110° C. for 1 hour. Upon cooling to room temperature, the reaction was concentrated. The residue was triturated with hexanes and then dried briefly under high vacuum. The solid residue (intermediate urea) was dissolved in freshly distilled tetrahydrofuran (2 mL), cooled to −3° C. and treated with potassium tert-butoxide (1.0 M in tetrahydrofuran; 0.65 mL; 0.65 mmol) (Aldrich). After 15 minutes in the cold, the reaction mixture was filtered through a silica gel pad (1 g) and washed with ethyl acetate. The filtrate was concentrated and purified by flash chromatography (Biotage, 40S, 20:80 to 40:60 ethyl acetate-hexanes gradient) to give (±)-7-chloro-4-ethyl-3-(4-methoxy-phenyl)-1-phenyl-3,4-dihydro-1H-pyrimido[4,5-d]pyrimidin-2-one as a solid. (Yield 0.14 g; 60.2%). The NMR of this material showed only two singlets for the pyrimidine proton indicating a mixture of the desired product and the corresponding 7-bromo compound.

Example 7e (±)-4-Ethyl-3-(4-methoxy-phenyl)-1-phenyl-7-phenylamino-3,4-dihydro-1H-pyrimido[4,5d]pyrimidin-2-one

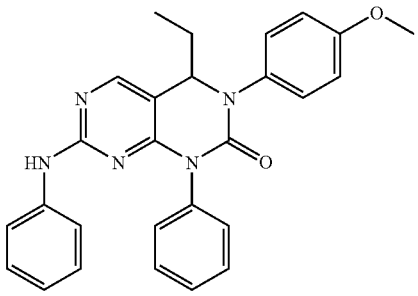

451.53

A mixture of (±)-7-chloro-4-ethyl-3-(4-methoxy-phenyl)-1-phenyl-3,4-dihydro-1H-pyrimido[4,5-d]pyrimidin-2-one (0.13 g; 0.34 mmol) (from Example 7d supra) and aniline (250 μL; 2.74 mmol) (Aldrich) was heated to 110° C. for 30 minutes. Upon cooling, the mixture was triturated and the resulting solid was dissolved in dichloromethane and washed with water and brine. The organic phase was dried over anhydrous sodium sulfate, filtered and concentrated. The crude material was purified by flash chromatography (Biotage, 12M; 35:65 to 50:50 ethyl acetate-hexanes gradient) and then crystallized from ethyl acetate-hexanes to give (±)-4-ethyl-3-(4-methoxy-phenyl)-1-phenyl-7-phenylamino-3,4-dihydro-1H-pyrimido[4,5d]pyrimidin-2-one as a white solid. (Yield 0.11 g; 73.6%).

Melting Point: 172–176° C. HR-MS(ES$^+$) m/z Calculated for $C_{27}H_{25}N_5O_2$ ([M+H]$^+$): 452.2081; Found: 452.2083.

Example 8a

2-Fluoro-4-methoxyaniline

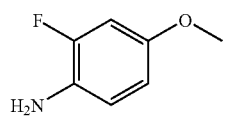

3-Fluoro-4-nitrophenol (10.17 g, 64.7 mmol) (Aldrich) was dissolved in dimethylformamide (210 mL). Potassium carbonate (45 g, 323 mmol) and methyl iodide (5 mL, 77.64 mmol) (Aldrich) were added and the reaction mixture was stirred at room temperature overnight. (thin layer chromatography: 20% ethyl acetate in hexanes showed complete conversion). The reaction mixture was filtered through a bed of Celite®, and concentrated under reduced pressure. The crude material was triturated with ether and insoluble materials were removed by filtration. The filtrate was concentrated under reduce pressure to afford an orange solid. This material (11.43 g) was dissolved in methanol (150 mL) and hydrogenated for 1.5 hours in a Parr apparatus at 50 psi, in the presence of 10% palladium on carbon (1.5 g) (Aldrich). (thin layer chromatography: 20% ethyl acetate in hexanes showed complete conversion). The reaction mixture was filtered through Celite®, washed with ethyl acetate, then concentrated under reduced pressure to give 2-fluoro-4-methoxyaniline as a solid. (Yield 3.81 g, 26.99 mmol).

Example 8b (±)-[1-(2,4-Dichloro-pyrimidin-5-yl)-ethyl]-(2-fluoro-4-methoxy-phenyl)-amine

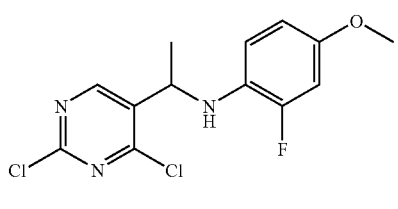

316.16

A mixture of (±)-2,4-dichloro-5-(1-bromoethyl)-pyrimidine (0.20 g; 0.79 mmol) (from Example 1c supra), N,N-diisopropylethyl-amine (140 µL; 0.80 mmol) (Aldrich) and 2-fluoro-4-methoxyaniline (0.11 g; 0.78 mmol) (from Example 8a supra) were combined in acetonitrile (3 mL) and stirred at room temperature overnight. The reaction was found to be incomplete and was then heated in an oil bath at 40–50° C. overnight. Upon cooling, the reaction was partitioned between ethyl acetate and water. The organic phase was washed with brine, dried over anhydrous sodium sulfate, filtered and concentrated. Purification by flash chromatography (Biotage, 40S; 10:90 to 20:80 ethyl acetate-hexanes gradient) gave (±)-[1-(2,4-dichloro-pyrimidin-5-yl)-ethyl]-(2-fluoro-4-methoxy-phenyl)-amine. (Yield 0.12 g; 49.1%).

Example 8c (±)-7-Chloro-3-(2-fluoro-4-methoxy-phenyl)-4-methyl-1-phenyl-3,4-dihydro-1H-pyrimido[4,5-d]pyrimidin-2-one

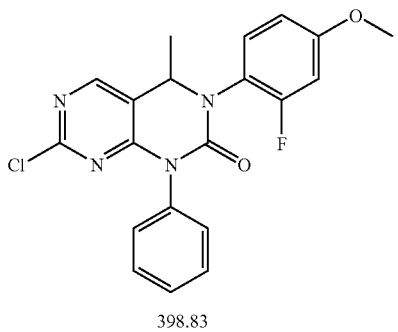

398.83

(±)-[1-(2,4-Dichloro-pyrimidin-5-yl)-ethyl]-(2-fluoro-4-methoxy-phenyl)-amine (0.45 g; 1.41 mmol) (from Example 8b supra) and phenyl isocyanate (165 µL; 1.52 mmol) (Aldrich) were combined in toluene (5 mL) and heated in an oil bath at 110–120° C. for 2.5 hours and then at 130° C. for 2.5 hours. After cooling, the reaction mixture was concentrated and triturated with hexanes. The solid residue was purified by flash chromatography (Biotage 40S; 30:70 ethyl acetate-hexanes) to give the intermediate (±)-1-[1-(2-chloropyrimidin-5-yl)-ethyl]-1-(2-fluoro-4-methoxy-phenyl)-3-phenyl-urea. (Yield 0.27 g; 43.2%).

This urea was suspended in freshly distilled tetrahydrofuran (3 mL) and cooled in an ice-brine bath. Potassium tert-butoxide (1.0 M in tetrahydrofuran; 0.64 mL; 0.64 mmol) (Aldrich) was added dropwise to the suspension over 5 minutes. The solid went into solution as the potassium tert-butoxide was added. After stirring for an additional 15 minutes in the cold, the reaction mixture was filtered through a bed of silica gel (1.75 g), eluting with 1:1 ethyl acetate-hexanes and then ethyl acetate. Purification by flash chromatography (Biotage 40S; 40:60 to 50:50 ethyl acetate-hexanes) gave (±)-7-chloro-3-(2-fluoro-4-methoxy-phenyl)-4-methyl-1-phenyl-3,4-dihydro-1H-pyrimido[4,5-d] pyrimidin-2-one. (Yield 0.22 g; 38% overall for two steps).

Example 8d (±)-3-(2-Fluoro-4-methoxy-phenyl)-4-methyl-1-phenyl-7-phenylamino-3,4-dihydro-1H-pyrimido[4,5-d]pyrimidin-2-one

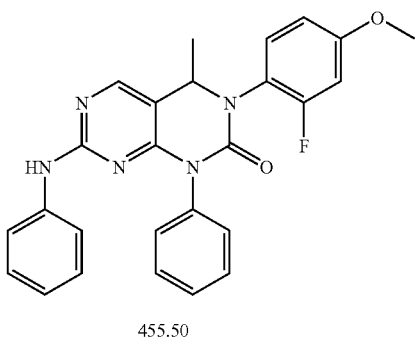

455.50

(±)-7-Chloro-3-(2-fluoro-4-methoxy-phenyl)-4-methyl-1-phenyl-3,4-dihydro-1H-pyrimido[4,5-d]pyrimidin-2-one (0.21 g; 0.53 mmol) (from Example 8c supra) and aniline (450 µL; 4.94 mmol) (Aldrich) were combined and heated at 110° C. for 1 hour. After cooling, the mixture was triturated with hexanes. The solid residue was dissolved in dichloromethane and washed with water and brine, dried over anhydrous sodium sulfate, filtered and concentrated. Purification by flash chromatography (Biotage 12M; 40:60 to 50:50 ethyl acetate-hexanes gradient) and then crystallization from dichloromethane-ether gave (±)-3-(2-fluoro-4-methoxy-phenyl)-4-methyl-1-phenyl-7-phenylamino-3,4-dihydro-1H-pyrimido[4,5-d]pyrimidin-2-one as a white solid. (Yield 0.20 g; 81.4%).

Melting Point: 242–250° C. HR-MS(ES$^+$) m/z Calculated for $C_{26}H_{22}FN_5O_2$ ([M+H]$^+$): 456.1831; Found: 456.1832.

Example 9a (±)-3-[7-Chloro-3-(2-fluoro-4-methoxy-phenyl)-4-methyl-2-oxo-3,4-dihydro-2H-pyrimido[4,5-d]pyrimidin-1-yl]-benzonitrile

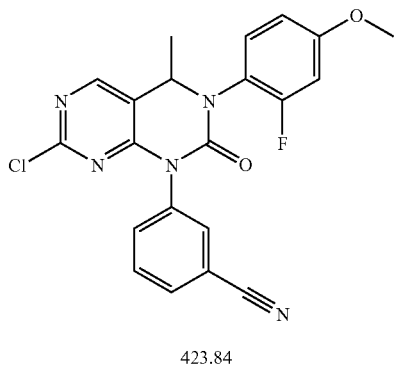

423.84

(±)-[1-(2,4-Dichloro-pyrimidin-5-yl)-ethyl]-(2-fluoro-4-methoxy-phenyl)-amine (1.15 g; 3.63 mmol) (from Example 8b supra) was combined with 3-cyanophenyl isocyanate (0.55 g; 3.81 mmol) (Aldrich) in toluene (10 mL) and heated in an oil bath at 110–115° C. for 2 hours and then up to 128° C. over the next 3 hours. Upon cooling to room temperature, the reaction was concentrated and triturated with hexanes. The crude material was purified by flash chromatography (Biotage, 40M; 50:50 ethyl acetate-hexanes) to give the intermediate (±)-1-[1-(2-chloro-pyrimidin-5-yl)-ethyl]-3-(3-cyano-pheny)-1-(2-fluoro-4-methoxy-phenyl)-urea. (Yield 1.20 g; 71.8%).

This urea was suspended in freshly distilled tetrahydrofuran (10 mL) and cooled in an ice-brine bath. Potassium tert-butoxide (1.0 M in tetrahydrofuran; 2.70 mL; 2.70 mmol) (Aldrich) was added dropwise to the suspension over 8 minutes. The reaction mixture was stirred for an additional 15 minutes in the cold and then filtered through a bed of silica gel (7–8 g), eluting with 1:1 ethyl acetate-hexanes and then ethyl acetate. Purification by flash chromatography (Biotage 40M; 40:60 to 50:50 ethyl acetate-hexanes) gave (±)-3-[7-chloro-3-(2-fluoro-4-methoxy-phenyl)-4-methyl-2-oxo-3,4-dihydro-2H-pyrimido[4,5-d]pyrimidin-1-yl]-benzonitrile as a white solid. (Yield 1.11 g; 66.8% overall for two steps).

Example 9b (±)-3-[3-(2-Fluoro-4-methoxy-phenyl)-4-methyl-2-oxo-7-phenylamino-3,4-dihydro-2H-pyrimido[4,5-d]pyrimidin-1-yl]-benzonitrile

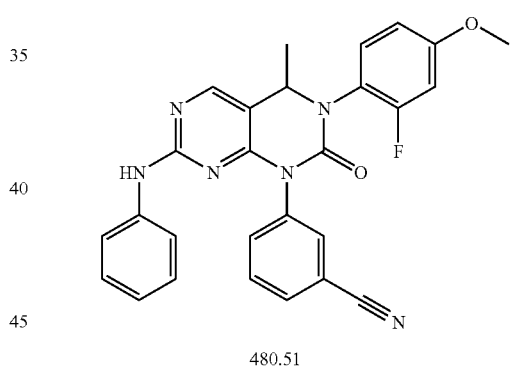

480.51

(±)-3-[7-Chloro-3-(2-fluoro-4-methoxy-phenyl)-4-methyl-2-oxo-3,4-dihydro-2H-pyrimido[4,5-d]pyrimidin-1-yl]-benzonitrile (1.03 g; 2.42 mmol) (from Example 9a supra) was combined with aniline (1.00 mL; 10.97 mmol) (Aldrich) and heated at 110° C. for 1 hour. At this point, the reaction mixture was a solid mass. Methanol (75 mL) was added and the mixture was heated at 110° C. for 20 minutes with vigorous stirring (solid remained insoluble). Upon cooling, the solid was collected, washed with methanol and then ether and dried under high vacuum to give (±)-3-[3-(2-fluoro-4-methoxy-phenyl)-4-methyl-2-oxo-7-phenylamino-3,4-dihydro-2H-pyrimido[4,5-d]pyrimidin-1-yl]-benzonitrile. (Yield 1.00 g; 85.6%). A portion of this material was recrystallized from dichloromethane-ether-petroleum ether for characterization and testing. (Yield 0.22 g).

Melting point: 223–228° C. HR-MS(ES$^+$) m/z Calculated for $C_{27}H_{21}FN_6O_2$ ([M+H]$^+$): 481.1783; Found: 481.1788.

Example 10

(±)-3-[3-(2-Fluoro-4-methoxy-phenyl)-4-methyl-2-oxo-7-phenylamino-3,4-dihydro-2H-pyrimido[4,5-d]pyrimidin-1-yl]-benzamide

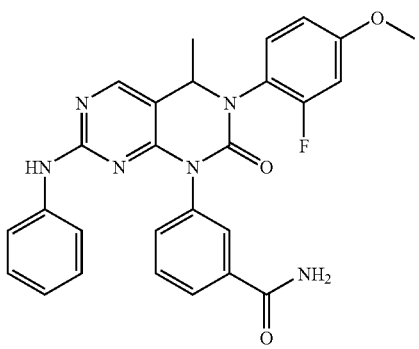

498.52

(±)-3-[3-(2-Fluoro-4-methoxy-phenyl)-4-methyl-2-oxo-7-phenylamino-3,4-dihydro-2H-pyrimido[4,5-d]pyrimidin-1-yl]-benzonitrile (0.80 g; 1.67 mmol) (from Example 9b supra) was dissolved in dimethyl sulfoxide (25 mL). Most of the material went into solution. Aqueous sodium hydroxide (1.0 N; 3.34 mL; 3.34 mmol) was added followed by hydrogen peroxide (30% in water; 0.51 mL, 4.99 mmol) at room temperature. After stirring for 45 minutes, water was added and a white solid precipitated out of solution. The solid was collected, washed with water and dried. Dissolution of the solid required significant volumes of dichloromethane-methanol-acetonitrile. The solvent mixture was then distilled off until solid began to crystallize out of solution. Cooling and filtration gave (±)-3-[3-(2-fluoro-4-methoxy-phenyl)-4-methyl-2-oxo-7-phenylamino-3,4-dihydro-2H-pyrimido[4,5-d]pyrimidin-1-yl]-benzamide as a white solid. (Yield 0.56 g; 67.6%).

Melting Point: 282–286° C. HR-MS(ES$^+$) m/z Calculated for $C_{27}H_{23}FN_6O_3$ ([M+H]$^+$): 499.1889; Found: 499.1894.

Example 11a (±)-1-(2,4-Dichloro-pyrimidin-5-yl)-2-methyl-propan-1-ol

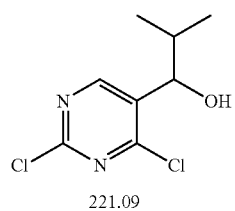

221.09

A solution of diisopropylamine (1.1 mL; 7.85 mmol) (Aldrich) and freshly distilled tetrahydrofuran (15 mL) was cooled to −78° C. n-Butyllithium (2.5M in hexanes; 3.1 mL; 7.75 mmol) (Aldrich) was added dropwise and stirring continued for 40 minutes to prepare a LDA solution. 2,4-Dichloropyrimidine (0.50 g; 3.37 mmol) (Aldrich) in tetrahydrofuran (3 mL) was then added dropwise to this freshly prepared LDA solution over 15 minutes. After stirring for 40 minutes, isobutyraldehyde (0.61 mL; 6.72 mmol) (Aldrich) was added over 6 minutes and stirring continued for another 30 minutes. The reaction was quenched with the addition of 25% aqueous ammonium chloride solution (20 mL) and then diluted with ethyl acetate and water. The organic phase was washed with a second portion of aqueous ammonium chloride solution and then brine, dried over anhydrous sodium sulfate, filtered, and concentrated. The residue was purified by flash chromatography (Biotage 40S; 10:90 to 15:85 ethyl acetate-hexanes gradient) to give (±)-1-(2,4-dichloro-pyrimidin-5-yl)-2-methyl-propan-1-ol. (Yield 0.25 g; 33.4%).

Example 11b (±)-5-(1-Bromo-2-methyl-propyl)-2,4-dichloro-pyrimidine

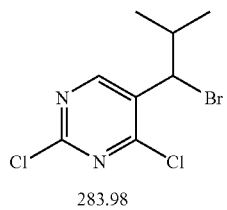

283.98

(±)-1-(2,4-Dichloro-pyrimidin-5-yl)-2-methyl-propan-1-ol (0.18 g; 0.83 mmol) (from Example 11a supra) was combined with N,N-diisopropyl-ethylamine (0.37 mL; 2.10 mmol) (Aldrich) and a small volume of dibromomethane (50 μL) (Aldrich) to help solubilize the mixture. Only a small amount of material remained insoluble. Neat phosphorus oxybromide (0.22 g; 0.85 mmol) (Aldrich) was added in one portion. Reaction mixture was stirred for 10 minutes and then partitioned between ethyl acetate and water. The organic phase was washed with brine, dried over anhydrous sodium sulfate, filtered and concentrated. Purification by flash chromatography (Biotage 12M) gave (±)-5-(1-bromo-2-methyl-propyl)-2,4-dichloro-pyrimidine as a colorless oil. (Yield 79.5 mg; 33.7%).

Example 11c (±)-[1-(2,4-Dichloro-pyrimidin-5-yl)-2-methyl-propyl]-(4-methoxy-phenyl)-amine

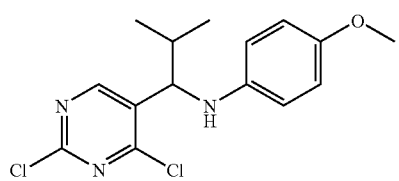

326.23

(±)-5-(1-Bromo-2-methyl-propyl)-2,4-dichloro-pyrimidine (88.7 mg; 0.312 mmol) (from Example 11b supra) was combined with potassium carbonate (47.4 mg; 0.34 mmol), potassium iodide (14.9 mg; 0.09 mmol) and p-anisidine (38.7 mg; 0.31 mmol) (Aldrich) and stirred at room temperature overnight. The reaction mixture was diluted with ethyl acetate and washed with water and then brine. The organic phase with dried over anhydrous sodium sulfate, filtered, and concentrated. Purification by flash chromatography (Biotage 12M; 10:90 to 30:70 ethyl acetate-hexanes gradient) gave (±)-[1-(2,4-dichloro-pyrimidin-5-yl)-2-methyl-propyl]-(4-methoxy-phenyl)-amine. (Yield 17.6 mg; 17.3%).

Example 11d (±)-7-Chloro-4-isopropyl-3-(4-methoxy-phenyl)-1-phenyl-3,4-dihydro-1H-pyrimido[4,5-d]pyrimidin-2-one

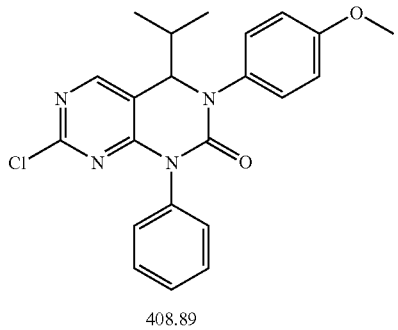

408.89

(±)-[1-(2,4-Dichloro-pyrimidin-5-yl)-2-methyl-propyl]-(4-methoxy-phenyl)-amine (35.0 mg; 0.107 mmol) (from Example 11c supra) and phenyl isocyanate (12.8 µL; 0.12 mmol) (Aldrich) were combined in toluene (0.6 mL), sealed and heated in a microwave reactor (SmithCreator™, 160 seconds to a maximum of 146° C., then 800 seconds at 160° C., and finally 600 seconds at 180° C.). The reaction was incomplete, and the mixture was concentrated and purified by flash chromatography (Biotage 12M; 20:80 ethyl acetate-hexanes) to give the intermediate (±)-1-[1-(2,4-dichloro-pyrimidin-5-yl)-2-methyl-propyl]-1-(4-methoxy-phenyl)-3-phenyl-urea. (Yield 24.0 mg).

This intermediate urea was dissolved in freshly distilled tetrahydrofuran (0.4 mL) and the resulting solution was cooled in an ice-brine bath. Potassium tert-butoxide (1.0 M in tetrahydrofuran; 60 µL; 0.06 mmol) (Aldrich) was added. The mixture was stirred for 15 minutes in the cold and then the bath was removed and stirring continued for another 5 minutes. The mixture was filtered through a bed of silica gel and washed with ethyl acetate. The filtrate was concentrated and dried to give (±)-7-chloro-4-isopropyl-3-(4-methoxy-phenyl)-1-phenyl-3,4-dihydro-1H-pyrimido[4,5-d]pyrimidin-2-one. (Yield 21.5 mg; 49% overall for two steps).

Example 11e (±)-4-Isopropyl-3-(4-methoxy-phenyl)-1-phenyl-7-phenylamino-3,4-dihydro-1H-pyrimido[4,5-d]pyrimidin-2-one

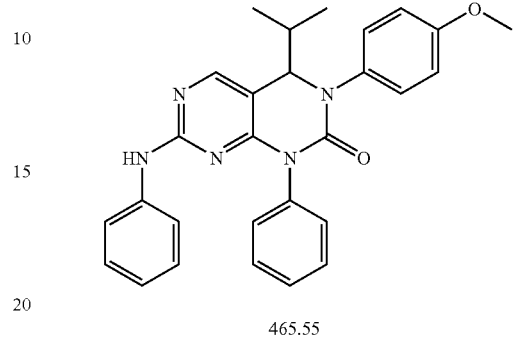

465.55

(±)-7-Chloro-4-isopropyl-3-(4-methoxy-phenyl)-1-phenyl-3,4-dihydro-1H-pyrimido[4,5-d]pyrimidin-2-one (22.0 mg; 0.054 mmol) (from Example 11d supra) and aniline (50 µL; 0.55 mmol) (Aldrich) were combined and heated in an oil bath at 100° C. for 1 hour. Upon cooling, the residue was triturated with hexanes and the supernatant was decanted off. The residue was dissolved in ethyl acetate and washed with water and then brine. The organic phase was mixed with silica gel, concentrated and subsequently purification by flash chromatography (Biotage 12M; 40:60 ethyl acetate-hexanes) and crystallization from dichloromethane-ether-petroleum ether gave (±)-4-isopropyl-3-(4-methoxy-phenyl)-1-phenyl-7-phenylamino-3,4-dihydro-1H-pyrimido[4,5-d]pyrimidin-2-one as a white solid. (Yield 14.8 mg; 59.1%). Melting Point: 229–235° C.

HR-MS(ES+) m/z Calculated for $C_{28}H_{27}N_5O_2$ ([M+H]+): 466.2238; Found: 466.2243. m/z Calculated for $C_{28}H_{27}N_5O_2$ ([M+Na]+): 488.2057; Found: 488.2059.

Example 12a (±)-(2-Chloro-5-methoxy-phenyl)-[1-(2,4-dichloro-pyrimidin-5-yl)-ethyl]-amine

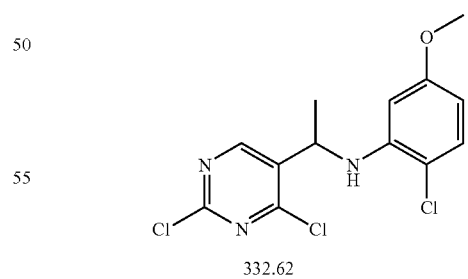

332.62

(±)-2,4-Dichloro-5-(1-bromoethyl)-pyrimidine (0.20 g; 0.79 mmol) (from Example 1c supra), N,N-diisopropylethylamine (0.40 mL; 2.27 mmol) (Aldrich) and 2-chloro-5-methoxyaniline hydrochloride (0.15 g; 0.77 mmol) (Aldrich) were combined (neat) and heated in an oil bath at 90° C. for 16 hours. Upon cooling, the mixture was taken up in ethyl acetate and washed with water and then brine. The organic phase was dried over anhydrous sodium sulfate, filtered, and concentrated. Purification by flash chromatography (Biotage 40M; 5:95 to 15:85 ethyl acetate-hexanes gradient) gave (±)-(2-chloro-5-methoxy-phenyl)-[1-(2,4-dichloro-pyrimidin-5-yl)-ethyl]-amine. (Yield 0.12 g; 45.9%).

Example 12b (±)-7-Chloro-3-(2-chloro-5-methoxy-phenyl)-4-methyl-1-phenyl-3,4-dihydro-1H-pyrimido[4,5-d]pyrimidin-2-one

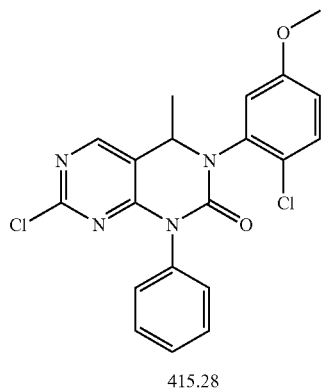

415.28

(±)-(2-Chloro-5-methoxy-phenyl)-[1-(2,4-dichloro-pyrimidin-5-yl)-ethyl]-amine (70 mg; 0.21 mmol) (from Example 12a supra) was combined with phenyl isocyanate (60 μL; 0.55 mmol) (Aldrich) and heated (neat) at 150° C. for 65 minutes. Thin layer chromatography analysis showed some unreacted starting material remained. Additional isocyanate (20 μL; 0.18 mmol) was added and the mixture heated at 150° C. for an additional 30 minutes. Upon cooling, hexanes was added. After stirring, the supernatant was decanted off and the residue dried to give the intermediate (±)-1-(2-chloro-5-methoxy-phenyl)-1-[1-(2-chloropyrimidin-5-yl)-ethyl]-3-phenyl-urea which contained about 20% starting material by HPLC.

This intermediate urea mixture was dissolved in tetrahydrofuran (0.5 mL) and cooled in an ice-brine bath. Potassium tert-butoxide (1.0 M in tetrahydrofuran; 200 μL; 0.20 mmol) was added dropwise. The mixture was stirred for 15 minutes in the cold and then the bath was removed and stirring continued for another 5 minutes. The mixture was filtered through a bed of silica gel (~1 g) and washed with ethyl acetate. The filtrate was combined with material from another reaction, concentrated and purified by flash chromatography (Biotage 12M; 20:80 to 40:60 ethyl acetate-hexanes) to give (±)-7-chloro-3-(2-chloro-5-methoxy-phenyl)-4-methyl-1-phenyl-3,4-dihydro-1H-pyrimido[4,5-d]pyrimidin-2-one. (Yield 45.8 mg; 40% overall for two experiments).

Example 12c (±)-3-(2-Chloro-5-methoxy-phenyl)-4-methyl-1-phenyl-7-phenylamino-3,4-dihydro-1H-pyrimido[4,5-d]pyrimidin-2-one

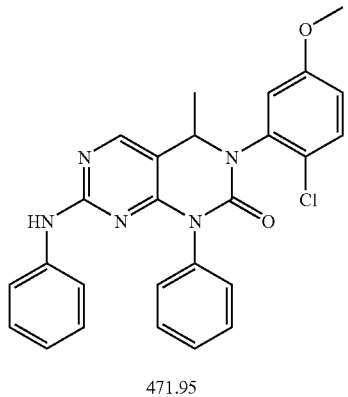

471.95

(±)-7-Chloro-3-(2-chloro-5-methoxy-phenyl)-4-methyl-1-phenyl-3,4-dihydro-1H-pyrimido[4,5-d]pyrimidin-2-one (0.20 g; 0.49 mmol) (from Example 12b supra) was combined with aniline (150 μL; 1.65 mmol) (Aldrich) and heated in an oil bath at 100° C. for about 70 minutes. Upon cooling, the residue was triturated with hexanes and then partitioned between ethyl acetate and water. The organic phase was washed with brine, dried over anhydrous sodium sulfate, filtered, and concentrated. The crude material was purified by flash chromatography (Biotage, 40M; 40:60 ethyl acetate-hexanes) to give (±)-3-(2-chloro-5-methoxy-phenyl)-4-methyl-1-phenyl-7-phenylamino-3,4-dihydro-1H-pyrimido[4,5-d]pyrimidin-2-one as a light yellow solid. (Yield 0.15 g; 63.7%).

HR-MS(ES$^+$) m/z Calculated for $C_{26}H_{22}ClN_5O_2$ ([M+H]$^+$): 472.1535; Found: 472.1537.

Example 13a (S)-(+)-3-(tert-Butyl-diphenyl-silanyloxy)-2-methyl-propionic acid

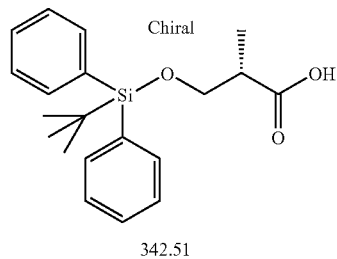

342.51

Methyl (S)-(+)-3-hydroxy-2-methylpropionate (1.06 g; 8.99 mmol) (Aldrich) was dissolved in dichloromethane (10 mL, dried over molecular sieves). Imidazole (0.85 g; 12.41 mmol) (Aldrich) and tert-butyl-diphenylsilyl chloride (2.30 mL; 8.85 mmol) (Aldrich) were added and the mixture was stirred at ambient temperature for 3 hours. The reaction was diluted with additional dichloromethane, washed with water

Example 13b (S)-tert-Butyl-2-isocyanato-propoxydiphenylsilane

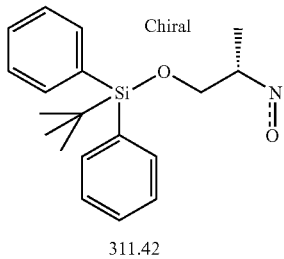

311.42

This material was generated in situ.

(S)-(+)-3-(tert-Butyl-diphenyl-silanyloxy)-2-methylpropionic acid (0.44 g; 1.20 mmol) (from Example 13a supra) was dissolved in dichloromethane (3 mL, dried over molecular sieves). Triethylamine (0.36 mL; 2.58 mmol) (Aldrich) was added and the solution was cooled in an ice-water bath. Ethyl chloroformate (0.16 mL; 1.63 mmol) (Aldrich) was added dropwise and the mixture was stirred in the cold for 1 hour. The mixture was then diluted with additional dichloromethane, washed with water and brine, dried over anhydrous sodium sulfate, filtered, and concentrated to yield (S)-(+)-3-(tert-butyl-diphenyl-silanyloxy)-2-methylpropionic acid chloride.

To a solution of the above acid chloride in acetone (4 mL) was added a solution of sodium azide (0.25 g; 3.85 mmol) in water (4 mL). The mixture was stirred for 10 minutes and then diluted with dichloromethane and water. The organic phase was washed with brine, dried over magnesium sulfate, filtered, and concentrated to yield (S)-(+)-3-(tert-butyl-diphenyl-silanyloxy)-2-methylpropionyl azide.

This azide was dissolved in toluene (2 mL) and heated in an oil bath at 120° C. to generate the desired (S)-tert-butyl-2-isocyanato-propoxydiphenylsilane by the Curtius rearrangement.

Example 13c

1-[2-(tert-Butyl-diphenyl-silanyloxy)-1-(S)-methyl-ethyl]-7-chloro-3-(4-methoxyphenyl)-4-methyl-3,4-dihydro-1H-pyrimido[4,5-d]pyrimidin-2-one

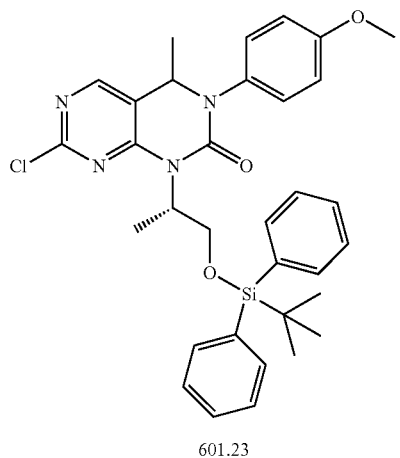

601.23

(S)-tert-Butyl-2-isocyanato-propoxy-diphenylsilane (generated in situ from 0.440 g, 1.20 mmol, of (S)-(+)-3-(tert-butyl-diphenyl-silanyloxy)-2-methylpropionic acid) (from Example 13b supra) in hot toluene (2 mL; 120° C.) was treated with a solution of (±)-[1-(2,4-dichloro-pyrimidin-5-yl)-ethyl]-(4-methoxy-phenyl)-amine (0.35 g; 1.10 mmol) (from Example 1d supra) in toluene (2 mL). The resulting solution was kept at 120° C. for 30 minutes, then cooled to room temperature and concentrated. The residue was dissolved in anhydrous tetrahydrofuran (4 mL) and cooled in an ice-brine bath. Potassium tert-butoxide (1.0 M in tetrahydrofuran; 1.2 mL; 1.20 mmol) (Aldrich) was added dropwise and stirring continued in the cold for 15 minutes. The mixture was filtered through a bed of silica gel and eluted with ethyl acetate. Further purification with flash chromatography (Biotage 40 M; 25:75 ethyl acetate-hexanes) gave 1-[2-(tert-butyl-diphenyl-silanyloxy)-1-(S)-methyl-ethyl]-7-chloro-3-(4-methoxy-phenyl)-4-methyl-3,4-dihydro-1H-pyrimido[4,5-d]pyrimidin-2-one as a mixture of diastereomers. (Yield 0.31 g; 46%). No separation of diastereomers was seen at this time.

--- and brine, dried over anhydrous sodium sulfate, filtered, and concentrated to yield methyl (S)-(+)-3-(tert-butyl-diphenylsilanyloxy)-2-methyl-propionate as an oil. (Yield 3.17 g; 98.8%).

This silyl-ether (3.15 g; 8.85 mmol) was dissolved in tetrahydrofuran-methanol (3:1) and saponified with aqueous sodium hydroxide (1.0 N; 10.0 mL; 10.0 mmol) overnight at ambient temperature. The reaction mixture was partitioned between ethyl acetate and water and acidified with 0.5 N hydrochloric acid to pH~4. The organic phase was washed with water and brine, dried over anhydrous sodium sulfate, filtered, and concentrated. Purification by flash chromatography (Biotage 40M; 25:75 ethyl acetate-hexanes) gave (S)-(+)-3-(tert-butyl-diphenyl-silanyloxy)-2-methylpropionic acid as a white solid. (Yield 2.06 g; 68.1%).

Example 13d 1-(2-Hydroxy-1-(S)-methyl-ethyl)-3-(4-methoxy-phenyl)-4-methyl-7-phenylamino-3,4-dihydro-1H-pyrimido[4,5-d]pyrimidin-2-one

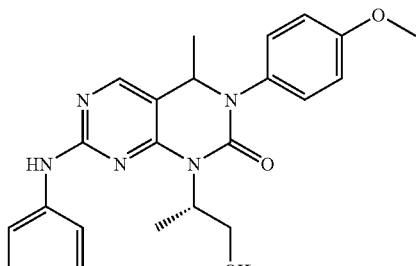

419.49

1-[2-(tert-Butyl-diphenyl-silanyloxy)-1-(S)-methyl-ethyl]-7-chloro-3-(4-methoxy-phenyl)-4-methyl-3,4-dihydro-1H-pyrimido[4,5-d]pyrimidin-2-one (0.286 g; 0.476 mmol) (from Example 13c supra) was combined with aniline (0.50 mL; 5.49 mmol) (Aldrich) and heated in an oil bath at 90° C. for 3 hours. The mixture was cooled to room temperature and partitioned between ethyl acetate and water. The organic phase was washed with brine, dried over anhydrous sodium sulfate, filtered, and concentrated. Flash chromatography (Biotage 40L; 40:60 ethyl acetate-hexanes) gave the silyl protected product. (Yield 0.29 g; 92%). There was a partial separation of the diastereomers noted at this point.

The above diastereomeric mixture of silyl protected products (80 mg; 0.12 mmol) were dissolved in anhydrous tetrahydrofuran (0.5 mL) and treated with tetrabutylammonium fluoride (1.0 M in tetrahydrofuran; 0.45 mL; 0.45 mmol) (Aldrich) at room temperature for approximately 7 hours. The reaction mixture was concentrated and the residue was partitioned between ethyl acetate and water. The organic phase was washed with brine, dried over anhydrous sodium sulfate, filtered and concentrated. Purification by flash chromatography (Biotage 12M; 60:40 to 75:25 ethyl acetate-hexanes gradient) followed by crystallization from ethyl acetate-hexanes yielded 1-(2-hydroxy-1-(S)-methyl-ethyl)-3-(4-methoxy-phenyl)-4-methyl-7-phenylamino-3,4-dihydro-1H-pyrimido[4,5-d]pyrimidin-2-one as a mixture of diastereomers. (Yield 38.9 mg; 79.4%).

Melting Point: 165–180° C. HR-MS(ES$^+$) m/z Calculated for $C_{23}H_{25}N_5O_3$ ([M+H]$^+$): 420.2030; Found: 420.2034.

Example 14a (R)-(−)-3-(tert-Butyl-diphenyl-silanyloxy)-2-methyl-propionic acid

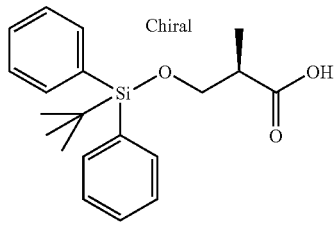

342.51

Methyl (R)-(−)-3-hydroxy-2-methylpropionate (30.81 g; 260.8 mmol) (Aldrich) was dissolved in dichloromethane (300 mL, dried over molecular sieves). Imidazole (25.11 g; 365.1 mmol) (Aldrich) and tert-butyl-diphenylsilyl chloride (68.00 mL; 261.5 mmol) (Aldrich) were added and the mixture was stirred at room temperature for 6 hours. The reaction was diluted with additional dichloromethane (300 mL), washed with water (2×150 mL) and brine (1×150 mL), dried over anhydrous sodium sulfate, filtered, and concentrated to yield methyl (R)-(−)-3-(tert-butyl-diphenyl-silanyloxy)-2-methyl-propionate as an oil. (Yield 94.3 g).

This crude silyl-ether (94.3 g) was dissolved in tetrahydrofuran-methanol (3:1, 875 mL)) and saponified with aqueous sodium hydroxide (1.0 N; 300.0 mL; 300.0 mmol) for 46 hours at room temperature. The reaction mixture was concentrated under reduced pressure to remove part of the organic solvents, and then diluted with ethyl acetate. After cooling in an ice-water bath, the mixture was acidified with 1 N aqueous hydrochloric acid (300 mL). The layers were separated and the organic phase was washed with water and brine, dried over anhydrous sodium sulfate, filtered, and concentrated to gave crude (R)-(−)-3-(tert-butyl-diphenyl-silanyloxy)-2-methylpropionic acid containing small amounts of ethyl acetate. Purity was estimated by NMR to be 95%. (Yield 90.4 g; 96%).

Example 14b (R)-tert-Butyl-2-isocyanato-propoxydiphenylsilane

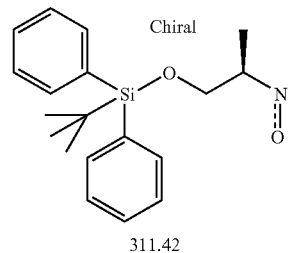

311.42

This material was generated in situ.

(R)-3-(tert-Butyl-diphenyl-silanyloxy)-2-methylpropionic acid (0.508 g; 1.48 mmol) (from Example 14a supra) was dissolved in dichloromethane (4 mL, dried over molecular sieves). Triethylamine (0.42 mL; 2.98 mmol) (Aldrich) was added and the solution was cooled in an ice-water bath. Ethyl chloroformate (0.17 mL; 1.78 mmol) (Aldrich) was added dropwise and the mixture was stirred in the cold for 50 minutes. The reaction mixture was diluted with additional dichloromethane and washed with water and then brine. The organic phase was dried over sodium sulfate and concentrated.

To a solution of this anhydride intermediate in acetone (5 mL) was added a solution of sodium azide (0.29 g; 4.41 mmol) in water (5 mL). The mixture was stirred at room temperature for 10 minutes and then diluted with additional dichloromethane and water. The organic phase was washed with brine, dried over magnesium sulfate and concentrated to yield (R)-3-(tert-butyl-diphenyl-silanyloxy)-2-methylpropionyl azide.

This azide was dissolved in toluene (~5 mL; dried over 4A molecular sieves) and heated in an oil bath at 120° C. Vigorous nitrogen gas evolution quickly resulted yielding the desired (R)-tert-butyl-2-isocyanato-propoxy-diphenylsilane by the Curtius rearrangement. This material was used without purification.

Example 14c

3-[2-tert-Butyl-diphenyl-silanyloxy-1-(R)-methyl-ethyl]-1-(R)-[1-(2,4-dichloropyrimidin-5-yl)-ethyl]-1-(4-methoxyphenyl)-urea

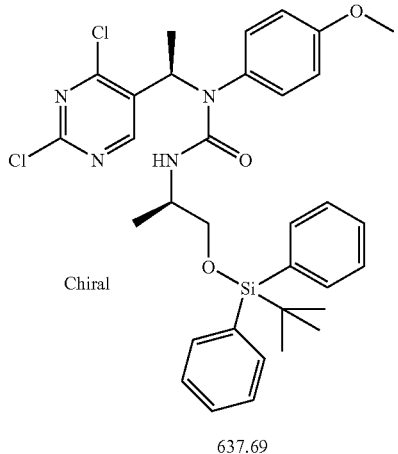

637.69

(R)-tert-Butyl-2-isocyanato-propoxy-diphenylsilane (generated in situ from 1.00 g, 2.861 mmol of (R)-3-(tert-butyl-diphenyl-silanyloxy)-2-methylpropionic acid) (from Example 14b supra) in hot toluene (4 mL) was treated with a toluene solution of (±)-[1-(2,4-dichloro-pyrimidin-5-yl)-ethyl]-(4-methoxy-phenyl)-amine (0.74 g; 2.38 mmol) (from Example 1d supra). The solution was heated at 115–120° C. for 3 hours and then cooled to room temperature. The crude reaction solution was purified by flash chromatography (multiple runs with Biotage 40L columns; 35:65 ethyl acetate-hexanes), which successfully separated the two diastereomers. The first eluting diastereomer, 3-[2-tert-butyl-diphenyl-silanyloxy-1-(R)-methyl-ethyl]-1-(R)-[1-(2,4-dichloropyrimidin-5-yl)-ethyl]-1-(4-methoxyphenyl)-urea, was obtained with an e.e. of 90–95%. (Yield 0.47 g; 25.7%).

Example 14d

3-[2-tert-Butyl-diphenyl-silanyloxy-1-(R)-methyl-ethyl]-1-(S)-[1-(2,4-dichloropyrimidin-5-yl)-ethyl]-1-(4-methoxyphenyl)-urea

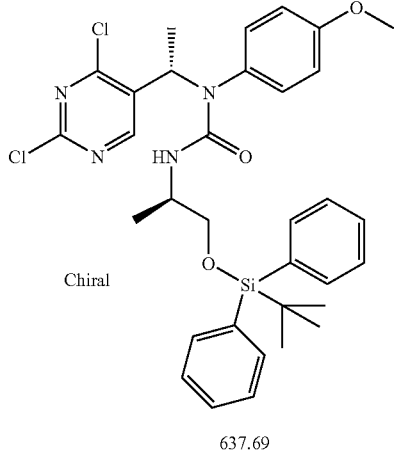

637.69

The second eluting diastereomer (from Example 14c supra), 3-[2-tert-butyl-diphenyl-silanyloxy-1-(R)-methyl-ethyl]-1-(S)-[1-(2,4-dichloropyrimidin-5-yl)-ethyl]-1-(4-methoxyphenyl)-urea, was obtained with an e.e. of 85–90%. (Yield 0.44 g; 24.1%).

Example 14e

1-[2-(tert-Butyl-diphenyl-silanyloxy)-1-(R)-methyl-ethyl]-7-chloro-3-(4-methoxy-phenyl)-(R)-4-methyl-3,4-dihydro-1H-pyrimido[4,5-d]pyrimidin-2-one

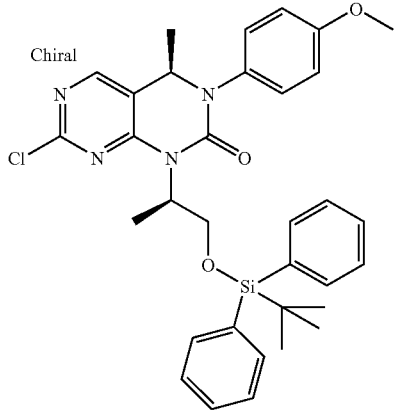

3-[2-tert-Butyl-diphenyl-silanyloxy-1-(R)-methyl-ethyl]-1-(R)-[1-(2,4-dichloropyrimidin-5-yl)-ethyl]-1-(4-methoxyphenyl)-urea (0.46 g, 96% purity; 0.69 mmol) (from Example 14c supra) was dissolved in anhydrous tetrahydrofuran (2 mL) and cooled in an ice-brine bath. Potassium tert-butoxide (1.0 M in tetrahydrofuran; 0.85 mL; 0.85 mmol) (Aldrich) was added dropwise over 5 minutes. The mixture was stirred in the cold for 15 minutes and then the bath was removed and stirring continued for another 5 minutes. The reaction mixture was filtered through a bed of silica gel and eluted with ethyl acetate. This crude product was purified by flash chromatography (Biotage 40M; 25:75 ethyl acetate-hexanes) to give 1-[2-(tert-butyl-diphenyl-silanyloxy)-1-(R)-methyl-ethyl]-7-chloro-3-(4-methoxy-phenyl)-(R)-4-methyl-3,4-dihydro-1H-pyrimido[4,5-d]pyrimidin-2-one. (Yield 0.32 g; 77.6%).

Example 14f 1-(2-Hydroxy-1-(R)-methyl-ethyl)-3-(4-methoxy-phenyl)-4-(R)-methyl-7-phenylamino-3,4-dihydro-1H-pyrimido[4,5-d]pyrimidin-2-one

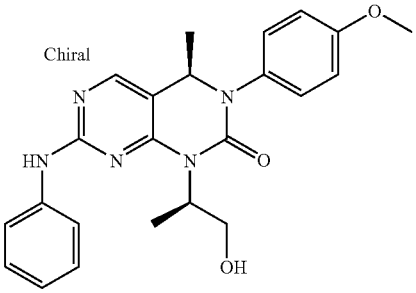

419.49

A solution of 1-[2-(tert-butyl-diphenyl-silanyloxy)-1-(R)-methyl-ethyl]-7-chloro-3-(4-methoxy-phenyl)-(R)-4-methyl-3,4-dihydro-1H-pyrimido[4,5-d]pyrimidin-2-one (0.32 g; 0.51 mmol) (from Example 14e supra) and aniline (0.12 mL; 1.32 mmol) (Aldrich) in toluene (0.25 mL, dried over molecular sieves) was heated in an oil bath at 110° C. for 1.75 hours. The reaction was diluted with ethyl acetate and washed with water and brine, dried over anhydrous sodium sulfate and concentrated. The crude material was purified by flash chromatography (Biotage 40L; 40:60 ethyl acetate-hexanes) to give 1-[2-(tert-butyl-diphenyl-silanyloxy)-1-(R)-methyl-ethyl]-3-(4-methoxy-phenyl)-4-(R)-methyl-7-phenylamino-3,4-dihydro-1H-pyrimido[4,5-d]pyrimidin-2-one. (Yield 0.30 g; 81.6%). This material showed an e.e. of ≧95%.

This intermediate (0.29 g; 0.41 mmol) was dissolved in anhydrous tetrahydrofuran (1.5 mL) and treated with tetrabutylammonium fluoride (1.0 M in tetrahydrofuran; 1.3 mL; 1.30 mmol) (Aldrich) at 50° C. for 2 hours. The reaction was cooled to room temperature and concentrated. The residue was taken up in ethyl acetate and washed with water (2) and brine, then dried over anhydrous sodium sulfate and concentrated. Purification by flash chromatography (Biotage 40M; 70:30 ethyl acetate-hexanes) followed by crystallization from ethyl acetate-hexanes gave 1-(2-hydroxy-1-(R)-methyl-ethyl)-3-(4-methoxy-phenyl)-4-(R)-methyl-7-phenylamino-3,4-dihydro-1H-pyrimido[4,5-d]pyrimidin-2-one as a white solid. (Yield 0.14 g; 79.1%). Melting Point: 158–162° C. HR-MS(ES$^+$) m/z Calculated for $C_{23}H_{25}N_5O_3$ ([M+H]$^+$): 420.2030; Found: 420.2035.

[α]=+53.3 (Rotation=+0.256; conc.=4.8 mg/mL (MeOH); λ=589).

Example 15a

1-[2-(tert-Butyl-diphenyl-silanyloxy)-1-(R)-methyl-ethyl]-7-chloro-3-(4-methoxy-phenyl)-4-(S)-methyl-3,4-dihydro-1H-pyrimido[4,5-d]pyrimidin-2-one

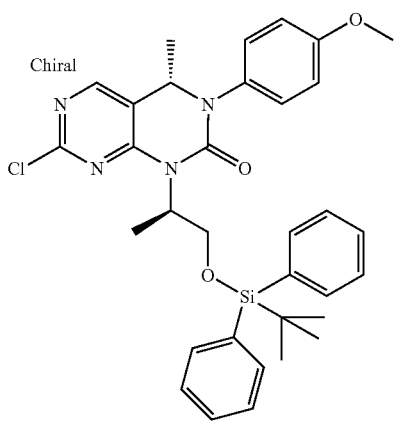

3-[2-tert-Butyl-diphenyl-silanyloxy-1-(R)-methyl-ethyl]-1-(S)-[1-(2,4-dichloropyrimidin-5-yl)-ethyl]-1-(4-methoxyphenyl)-urea (0.44 g, 96%; 66 mmol) (from Example 14d supra) was dissolved in anhydrous tetrahydrofuran (1.5 mL) and cooled in an ice-brine bath. Potassium tert-butoxide (1.0 M in tetrahydrofuran; 0.80 mL; 0.80 mmol) (Aldrich) was added dropwise over 5 minutes. The mixture was stirred in the cold for 15 minutes and then the bath was removed and stirring continued for another 5 minutes. The reaction mixture was filtered through a bed of silica gel and eluted with ethyl acetate. This crude product was purified by flash chromatography (Biotage 40M; 30:70 ethyl acetate-hexanes) to give 1-[2-(tert-butyl-diphenyl-silanyloxy)-1-(R)-methyl-ethyl]-7-chloro-3-(4-methoxy-phenyl)-4-(S)-methyl-3,4-dihydro-1H-pyrimido[4,5-d]pyrimidin-2-one. (Yield 0.29 g; 72.8%).

Example 15b 1-(2-Hydroxy-1-(R)-methyl-ethyl)-3-(4-methoxy-phenyl)-4-(S)-methyl-7-phenylamino-3,4-dihydro-1H-pyrimido[4,5-d]pyrimidin-2-one

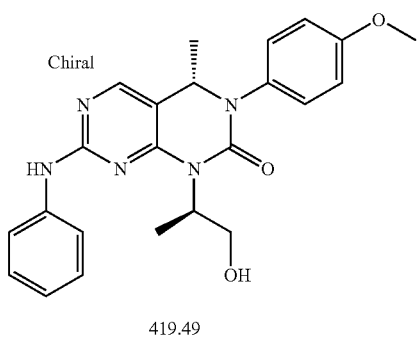

419.49

A solution of 1-[2-(tert-butyl-diphenyl-silanyloxy)-1-(R)-methyl-ethyl]-7-chloro-3-(4-methoxy-phenyl)-4-(S)-methyl-3,4-dihydro-1H-pyrimido[4,5-d]pyrimidin-2-one (0.28 g; 0.45 mmol) (from Example 15a supra) and aniline (0.10 mL; 1.21 mmol) (Aldrich) in toluene (0.25 mL, dried over molecular sieves) was heated in an oil bath at 110° C. for 2 hours. The reaction was diluted with ethyl acetate and washed with water and brine, dried over anhydrous sodium sulfate and concentrated. The crude material was purified by flash chromatography (Biotage 40L; 40:60 ethyl acetate-hexanes) to give 1-[2-(tert-butyl-diphenyl-silanyloxy)-1-(R)-methyl-ethyl]-3-(4-methoxy-phenyl)-4-(S)-methyl-7-phenylamino-3,4-dihydro-1H-pyrimido[4,5-d]pyrimidin-2-one. (Yield 0.23 g; 73.0%). This material showed an e.e. of ~95%.

This intermediate (0.23 g; 0.32 mmol) was dissolved in anhydrous tetrahydrofuran (1.0 mL) and treated with tetrabutylammonium fluoride (1.0 M in tetrahydrofuran; 0.9 mL; 0.90 mmol) (Aldrich) at 50° C. for 2 hours. The reaction was cooled to room temperature and concentrated. The residue was taken up in ethyl acetate and washed with water (2) and brine, then dried over anhydrous sodium sulfate and concentrated. Purification by flash chromatography (Biotage 40M; 7:11:2 ethyl acetate-dichloromethane-hexanes with 1% methanol) followed by crystallization from ethyl acetate-hexanes gave 1-(2-hydroxy-1-(R)-methyl-ethyl)-3-(4-methoxy-phenyl)-4-(S)-methyl-7-phenylamino-3,4-dihydro-1H-pyrimido[4,5-d]pyrimidin-2-one as a white solid. (Yield 0.08 g; 59.3%).

Melting Point: 195–198° C. HR-MS(ES$^+$) m/z Calculated for $C_{23}H_{25}N_5O_3$ ([M+H]$^+$): 420.2030; Found: 420.2032. [α]=−62.80 (Rotation=−0.201; conc.=3.2 mg/mL (MeOH); λ=589).

Example 16

1-[1-(2,4-Dichloro-pyrimidin-5-yl)-ethyl]-1-(4-methoxy-phenyl)-3-[1-(S)-phenyl-ethyl]-urea

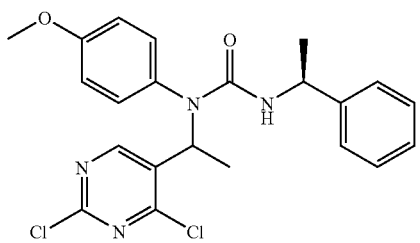

445.352

A mixture of [1-(2,4-dichloro-pyrimidin-5-yl)-ethyl]-(4-methoxy-phenyl)-amine (378 mg, 1.27 mmol) (from Example 1d supra) and (S)-(−)-α-methylbenzyl isocyanate (205 mg, 1.39 mmol) (Aldrich) in toluene (5 mL) was stirred at 100° C. for 16 hours. After cooling to room temperature the reaction mixture was purified by passing through silica gel and eluting with hexanes-ethyl acetate (1:1) to give 1-[1-(2,4-dichloro-pyrimidin-5-yl)-ethyl]-1-(4-methoxy-phenyl)-3-[1-(S)-phenyl-ethyl]-urea as two separable diastereomers. Less polar diastereomer (thin layer chromatography in hexanes-ethyl acetate, 1:1) (Yield 270 mg, 47.8%) and more polar diastereomer (Yield 284 mg, 50.3%).

Example 17

7-Chloro-3-(4-methoxy-phenyl)-4-methyl-1-[1-(S)-phenyl-ethyl]-3,4-dihydro-1H-pyrimido[4,5-d]pyrimidin-2-one

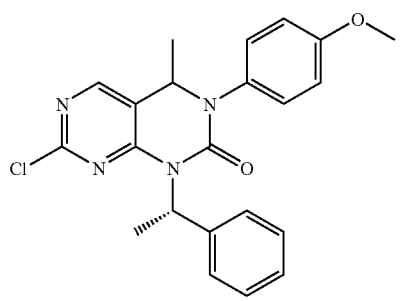

A solution of 1-[1-(2,4-dichloro-pyrimidin-5-yl)-ethyl]-1-(4-methoxy-phenyl)-3-[1-(S)-phenyl-ethyl]-urea (less polar diastereomer, 250 mg, 0.56 mmol) (from Example 16 supra) in tetrahydrofuran (5 mL). cooled to 5° C. was treated with potassium tert-butoxide (1.0 M solution in tetrahydrofuran, 0.62 mL, 0.62 mmol). After stirring at 5° C. for 15 minutes and then at room temperature for another 15 minutes, reaction mixture was diluted with ethyl acetate (20 mL) and was washed with water (2×10 mL) and dried over MgSO$_4$. Solvent was evaporated under reduced pressure to give crude 7-chloro-3-(4-methoxy-phenyl)-4-methyl-1-[1-(S)-phenyl-ethyl]-3,4-dihydro-1H-pyrimido[4,5-d]pyrimidin-2-one which was used directly in the following step. (308 mg, contains some solvent).

Example 18

3-(4-Methoxy-phenyl)-4-methyl-7-phenylamino-1-[1-(S)-phenyl-ethyl]-3,4-dihydro-1H-pyrimido[4,5-d]pyrimidin-2-one

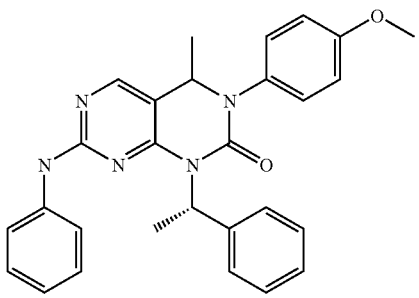

465.560

A suspension of crude 7-chloro-3-(4-methoxy-phenyl)-4-methyl-1-[1-(S)-phenyl-ethyl)-3,4-dihydro-1H-pyrimido[4,5-d]pyrimidin-2-one (308 mg, from 0.56 mmol) (from Example 17 supra) in aniline (0.195 mL) (Aldrich) was stirred at 100° C. for 3 hours. Reaction mixture was then cooled to room temperature, diluted with toluene (3 mL) and purified by column chromatography (silica gel) eluting with hexanes-ethyl acetate (1:1) to give 3-(4-methoxy-phenyl)-4-methyl-7-phenylamino-1-[1-(S)-phenyl-ethyl]-3,4-dihydro-1H-pyrimido[4,5-d]pyrimidin-2-one. (Yield 140 mg, 53.7%).

Example 19

(±)-N-[6-(4-Methoxy-phenyl)-5-methyl-7-oxo-8-phenyl-5,6,7,8-tetrahydro-pyrimido[4,5-d]pyrimidin-2-yl]-N-phenyl-acetamide

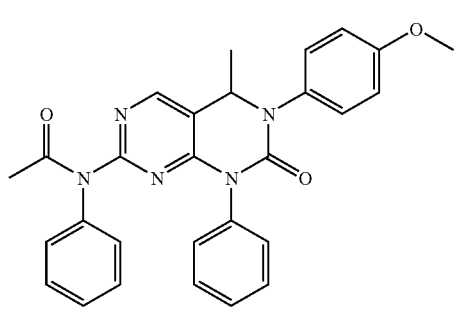

479.54

To a suspension of (±)-3-(4-methoxy-phenyl)-4-methyl-1-phenyl-7-phenylamino-3,4-dihydro-1H-pyrimido[4,5-d]pyrimidin-2-one (500 mg, 1.14 mmol) (from Example 1g supra) in pyridine (1 mL) (Fisher) was added acetic anhydride (1.0 mL) followed by addition of 4-(dimethylamino)pyridine (25 mg) (Aldrich) in one portion. The reaction mixture was heated to 90° C. for 5 hours until no starting material was detectable by TLC analysis. The reaction mixture was quenched with water and extracted with ethyl acetate (3×50 mL). The combined organic extracts were successively washed with water (10 mL) and brine (10 mL), dried over anhydrous sodium sulfate, filtered, and concentrated under reduced pressure to give the crude product which was purified by flash chromatography to give (±)-N-[6-(4-methoxy-phenyl)-5-methyl-7-oxo-8-phenyl-5,6,7,8-tetrahydro-pyrimido[4,5-d]pyrimidin-2-yl]-N-phenyl-acetamide. (Yield 373 mg, 68.0%).

Example 20a trans-4-(tert-Butyl-dimethyl-silanyloxy)-cyclohexylamine

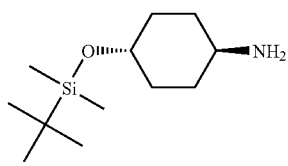

To a solution of trans-4-aminocyclohexanol (5.0 g, 43.4 mmol) (TCI US) in dichloromethane (100 mL) was added imidazole (14.78 g, 0.22 mol) (Aldrich) and tert-butyidimethylsilyl chloride (19.63 g, 0.13 mol) (Avocardo Research Chemicals). The reaction mixture was stirred at room temperature for 1 day. It was concentrated under reduced pressure, and the residue was diluted with ethyl acetate (100 mL) and water (100 mL). The organic layer was washed with 1 N sodium hydroxide solution, water and brine, dried (MgSO$_4$), filtered and concentrated to give crude trans-4-(tert-butyl-dimethyl-silanyloxy)-cyclohexylamine which was used in the next step without further purification. (Yield 7.62 g, 76.5%).

Example 20b (±)-1-(trans-4-Hydroxy-cyclohexyl)-3-(4-methoxyphenyl)-4-methyl-7-phenylamino-3,4-dihydro-1H-pyrimido[4,5-d]pyrimidin-2-one

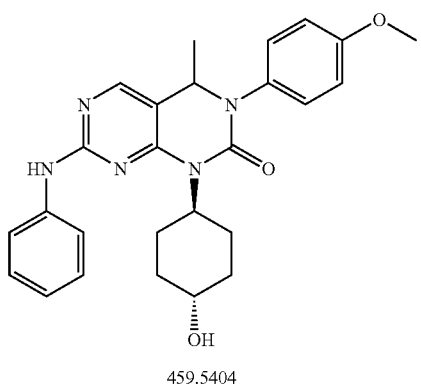

459.5404

To a solution of trans-4-(tert-butyl-dimethyl-silanyloxy)-cyclohexylamine (500 mg, 2.20 mmol) (from Example 20a supra) and triethylamine (1.52 mL, 10.90 mmol) (Aldrich) in dichloromethane (15 mL) was added a 20% phosgene in toluene solution (3.2 mL, 6.50 mmol) (Fluka) at 0° C. The resulting mixture was stirred for 15 minutes, then filtered and the filtrate was concentrated to a residue that was distilled at 110° C. under high vacuum using a Kugelrohr apparatus to give trans-4-(tert-butyl-dimethyl-silanyloxy)-cyclohexyl isocyanate (485 mg) as a colorless liquid.

This intermediate isocyanate (223 mg, 0.87 mmol) was dissolved in anhydrous tetrahydrofuran (approx. 3 mL) and added via a cannula to a solution of (±)-[1-(2,4-dichloropyrimidin-5-yl)-ethyl]-(4-methoxyphenyl)-amine (204 mg, 0.67 mmol) (from Example 1d supra) and n-butyllithium (2.5 M solution in hexanes, 295 µL, 0.74 mmol) (Aldrich) in anhydrous tetrahydrofuran (15 mL) at −78° C. The resulting reaction mixture was allowed to stir and warm up to room temperature within 2.25 hours and then partitioned between ethyl acetate and water. The ethyl acetate layer was removed, dried over sodium sulfate, filtered and concentrated to a residue that was purified by chromatography with a silica gel column and a 0–40% ethyl acetate in hexanes gradient to give a brownish foam. This intermediate was then dissolved in aniline (3 mL) (Aldrich) and the resulting solution was heated at 90° C. for 8 hours. After cooling, the reaction mixture was directly applied on a silica gel column and purified by chromatography with a 0–50% ethyl acetate in hexanes gradient. This purified intermediate was then dissolved in a 20% solution of trifluoroacetic acid in dichloromethane (5 mL) and water (300 µL) at 0° C. After stirring for 30 minutes at 0° C. the mixture was partitioned between ethyl acetate and 0.5N aqueous sodium hydroxide solution. The pH of the aqueous layer was adjusted to 13 by adding solid sodium hydroxide. The organic phase was then separated, dried over sodium sulfate, filtered and concentrated and the resulting residue was purified on a silica gel column with a 0–100% ethyl acetate in hexanes to product. This purified product was dissolved in dichloromethane and precipitated with excess pentane to give (±)-1-(trans-4-hydroxy-cyclohexyl)-3-(4-methoxy-phenyl)-4-methyl-7-phenylamino-3,4-dihydro-1H-pyrimido[4,5-d]pyrimidin-2-one as a white solid. (Yield 121 mg, 9%). HRMS m/z calcd for $C_{26}H_{29}N_5O_3$ ([M+H]$^+$): 460.2343. Found: 460.2347.

Example 21

The following compounds can be prepared by methods analogous to those herein disclosed above:

Example 21a

1-[(1R,3R)-3-Hydroxy-cyclopentyl]-3-(4-methoxyphenyl)-4—(S)-methyl-7-phenylamino-3,4-dihydro-1H-pyrimido[4,5-d]pyrimidin-2-one

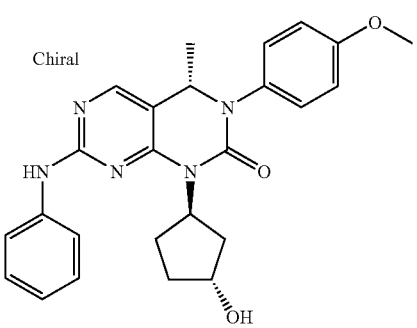

Example 21b

1-[(1S,3S)-3-Hydroxy-cyclopentyl]-3-(4-methoxy-phenyl)-4-(S)-methyl-7-phenylamino-3,4-dihydro-1H-pyrimido[4,5-d]pyrimidin-2-one

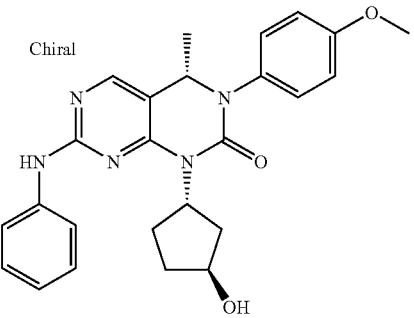

Example 21c 7-(4-Fluoro-phenylamino)-1-[(1R,3R)-3-hydroxy-cyclopentyl)]-3-(4-methoxy-phenyl)-4-(S)-methyl-3,4-dihydro-1H-pyrimido[4,5-d]pyrimidin-2-one

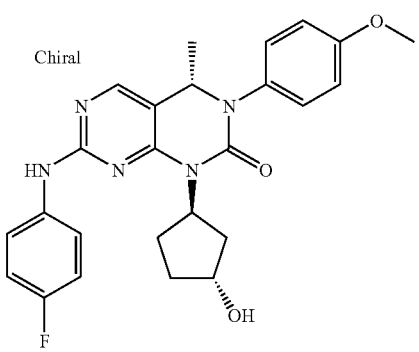

Example 21d 7-(4-Fluoro-phenylamino)-1-[(1S,3S)-3-hydroxy-cyclopentyl)]-3-(4-methoxy-phenyl)-4-(S)-methyl-3,4-dihydro-1H-pyrimido[4,5-d]pyrimidin-2-one

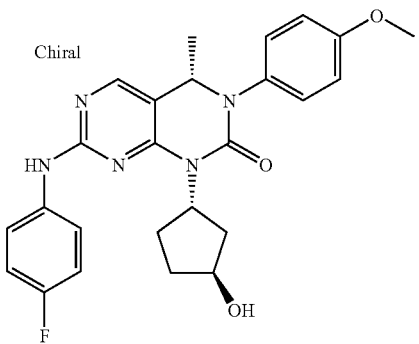

Example 21e 7-(4-Fluoro-phenylamino)-1-(2-hydroxy-1-(R)-methyl-ethyl)-3-(4-methoxy-phenyl)-4-(S)-methyl-3,4-dihydro-1H-pyrimido[4,5-d]pyrimidin-2-one

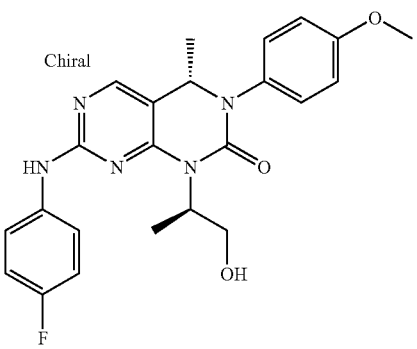

Example 21f 3-(4-Chloro-phenyl)-7-(4-fluoro-phenylamino)-1-(2-hydroxy-1-(R)-methyl-ethyl)-4-(S)-methyl-3,4-dihydro-1H-pyrimido[4,5-d]pyrimidin-2-one

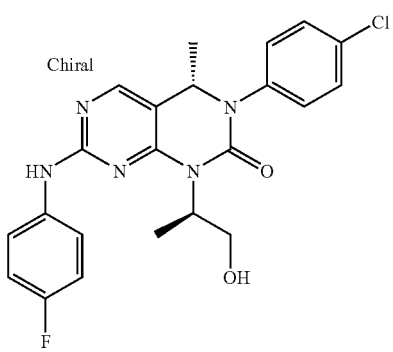

Example 21g 3-(4-Chloro-2-fluoro-phenyl)-7-(4-fluoro-phenylamino)-1-(2-hydroxy-1-(R)-methyl-ethyl)-4-(S)-methyl-3,4-dihydro-1H-pyrimido[4,5-d]pyrimidin-2-one

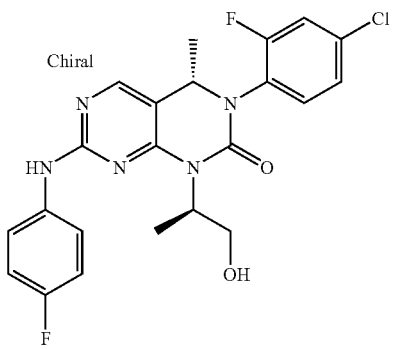

Example 21h 3-(4-Chloro-phenyl)-1-(2-hydroxy-1-(R)-methyl-ethyl)-4-(S)-methyl-7-phenylamino-3,4-dihydro-1H-pyrimido[4,5-d]pyrimidin-2-one

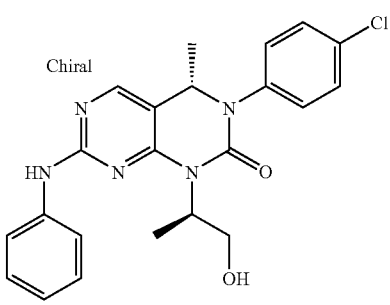

Example 21i 3-(4-Chloro-2-fluoro-phenyl)-1-(2-hydroxy-1-(R)-methyl-ethyl)-4-(S)-methyl-7-phenylamino-3,4-dihydro-1H-pyrimido[4,5-d]pyrimidin-2-one

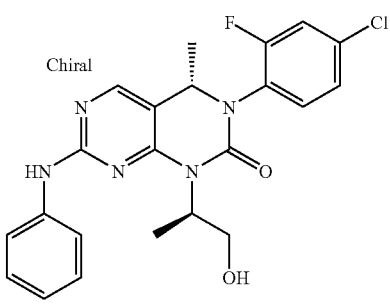

Example 21j 3-(4-Chloro-phenyl)-1-(3-hydroxy-2-(S)-methyl-propyl)-4-(S)-methyl-7-phenylamino-3,4-dihydro-1H-pyrimido[4,5-d]pyrimidin-2-one

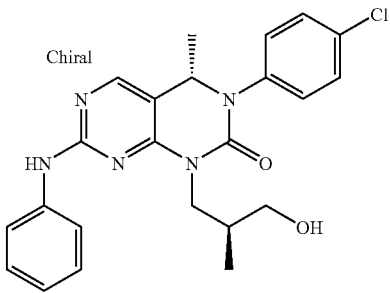

Example 21k 3-(4-Chloro-2-fluoro-phenyl)-1-(3-hydroxy-2-(S)-methyl-propyl)-4-(S)-methyl-7-phenylamino-3,4-dihydro-1H-pyrimido[4,5-d]pyrimidin-2-one

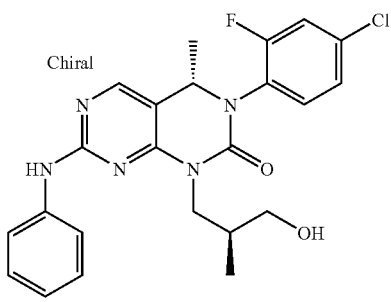

Antiproliferative Activity

The antiproliferative activity of the compounds of the invention is demonstrated below in Examples 22 and 23. These activities indicate that the compounds of the present invention are useful in treating cancer, in particular solid tumors such as breast, lung, prostate and colon tumors, more particularly breast and colon tumors.

Example 22

Kinase Assays

To determine inhibition of KDR, FGFR, EGFR, and PDGFR activity, kinase assays were conducted using an HTRF (Homogeneous Time Resolved Fluorescence) assay. This assay is described in A. J. Kolb et. al., Drug Discovery Today, 1998, 3(7), p 333.

Prior to kinase reaction, recombinant EEE-tagged KDR was activated in the presence of activation buffer (50 mM HEPES, pH 7.4, 1 mM DTT, 10% glycerol, 150 mM NaCl, 0.1 mM EDTA, 26 mM $MgCl_2$, and 4 mM ATP). The enzyme was incubated at 4° C. for 1 hour.

Kinase activity assays were performed in 96-well polypropylene plates (Falcon) with a total volume of 90 μL in each well. Each well contained 1 μM KDR substrate (Biotin-EEEEYFELVAKKKK), 1 nM activated KDR, and a test compound with one of 8 assay concentrations ranging from 100 μM to 128 pM (1:5 serial dilution). The kinase activity assay was done in the presence of 100 mM HEPES, pH 7.4, 1 mM DTT, 0.1 mM $Na_2VO_4$, 25 mM $MgCl_2$, 50 mM NaCl (from KDR stock solution), 1% DMSO (from compound), 0.3 mM ATP (at $K_m$ concentration) and 0.02% BSA. The reaction was incubated at 37° C. for 30 minutes. To stop the KDR reaction, 72 μL of reaction mixture was transferred into a STOP plate containing 18 μL of revelation buffer (20 mM EDTA, 50 mM HEPES, pH 7.4, 0.02% BSA, 10 nM Eu-labelled anti-pY antibody (final conc. 2 nM), and 100 nM streptavidin (final conc. 20 nM)). After mixing, 35 μL of solution was transferred into duplicate wells of a 384-well black plate (Costar), and read at 615/665 nm on a Wallac Victor 5 reader.

FGFR, EGFR, and PDGFR activity assays were carried out as described above for the KDR activity assay with the following differences. GST-tagged FGFR enzyme was activated at room temperature for 1 hour in the following activation buffer: 100 mM HEPES, pH 7.4, 50 mM NaCl, 20 mM $MgCl_2$, and 4 mM ATP. The kinase activity assay was performed with 1 µM substrate (Biotin-EEEEYFELV), 1.5 nM activated FGFR, and test compound in the presence of 100 mM HEPES, 1 mM DTT, 0.4 mM $MgCl_2$, 0.4 mM $MnCl_2$, 50 mM NaCl, 1% DMSO, 10 µM ATP ($K_m$=8.5 µM for FGFR), 0.1 mM $Na_2VO_4$, and 0.02% BSA, in a total volume of 90 µL. The rest of the assay was performed in the same manner as KDR assay.

The EGFR kinase activity assay was performed with 1 µM substrate (Biotin-EEEEYFELV), 1.5 nM EGFR, test compounds, 100 mM HEPES, pH 7.4, 1 mM DTT, 5 mM $MgCl_2$, 2 mM $MnCl_2$, 1% DMSO, 0.5 µM ATP ($K_m$ for EGFR), 0.1 mM $Na_2VO_4$, and 0.02% BSA. The rest of the assay was performed in the same manner as the KDR assay.

The PDGFR kinase activity assay was performed with 1 µM substrate (Biotin-EEEEYFELV), 1.0 nM PDGFR, test compounds, 100 mM HEPES, pH 7.4, 1 mM DTT, 5 mM $MgCl_2$, 2 mM $MnCl_2$, 1% DMSO, 2.3 µM ATP ($K_m$ for PDGFR), 0.1 mM $Na_2VO_4$, and 0.02% BSA. The rest of the assay was performed in the same manner as the KDR assay.

Compound $IC_{50}$ values were determined from duplicate sets of data, and calculated by using Excel and fitting data to equation $Y=[(a-b)/\{1+(X/c)^d\}]+b$, where a and b are enzyme activity in the presence of no test inhibitor compound and an infinite amount of inhibitor test compound, respectively, c is the $IC_{50}$ and d is the hill constant of the compound response. The $IC_{50}$ value is the concentration of test compound that reduces by 50% the enzyme activity under the test conditions described.

The results of the foregoing in vitro experiments, including $IC_{50}$ values, are set forth in Table 1 below.

TABLE 1

$IC_{50}$ (µM) - Enzyme Inhibition Assays

| Example | KDR | FGFR | EGFR | PDGFR |
|---|---|---|---|---|
| 1g | <10 | <10 | <10 | <10 |
| 4b | <10 | <10 | <10 | <10 |
| 2 | <10 | <10 | <10 | <10 |
| 3 | <10 | <10 | <10 | <10 |
| 5b | <10 | <10 | <10 | <10 |
| 6 | <10 | <10 | <10 | <10 |
| 7e | <10 | <10 | <10 | <10 |
| 8d | <10 | <10 | <10 | <10 |
| 9b | <10 | <10 | <10 | <10 |
| 10 | <10 | <10 | <10 | <10 |
| 11e | >10 | >10 | <10 | >10 |
| 12c | <10 | <10 | <10 | <10 |
| 14f | <10 | <10 | <10 | <10 |
| 15b | <10 | <10 | <10 | <10 |
| 18 | <10 | <10 | <10 | <10 |
| 19 | <10 | <10 | <10 | <10 |
| 20b | <10 | <10 | <10 | <10 |

Example 23

VEGF and FGF-Stimulated HUVEC Proliferation Assays

The antiproliferative activity of test compounds of this invention in cell-based assays was evaluated by BrdU assay using the BrdU kit (Roche Biochemicals 1-647-229). Human umbilical vein endothelial cells (HUVEC, Clonetics CC-2519) were cultured in EGM-2 (Clonetics CC-3162) medium and seeded at 10000 cells per well in a volume of 200 µL of EGM-2 (Clonetics CC-3162) media in a 96-well flat bottom plates (Costar 3595) overnight. After 24 hours of growth at 37° C. with 5% $CO_2$, the incubation media was removed slowly by aspiration and the content of each well was washed with 300 µL pre-warmed EBM-2 (Clonetics CC-3156) containing 50 µg per mL of gentamycin and 50 ng per mL of amphotercin-B (Clonetics CC-4083). Subsequently, the remaining media was again aspirated and replaced with 160 µL per well of serum starvation media (EBM-2 supplemented with 1% heat inactivated FBS (Clonetics CC-4102), 50 µg per mL gentamycin and 50 ng per mL of amphotercin-B (Clonetics CC-4083), 10 units per mL of Wyeth-Ayerst heparin (NDC0641-0391-25), and 2 mM L-glutamine (GIBCO 25030-081). After serum starving the cells for 24 hours, 20 µL of test compound at 10× test concentration in serum starvation medium with 2.5% DMSO was added to the appropriate wells. The control wells contained 20 µL of serum starvation medium with 2.5% DMSO. Plates were returned to the incubator for 2 hours. After pre-incubating the cells with the test compounds for 2 hours, 20 µL of growth factors at 10× assay concentration diluted in serum starvation media, FGF at 50 ng per mL, or VEGF (R&D systems 293-VE) at 200 ng per mL were added. The final concentration of FGF in the assay was 5 ng per mL and the final concentration of VEGF in the assays was 20 ng per mL. The growth factor free control wells had 20 µL per well of serum starvation media with the same amount of BSA as the wells with growth factors. The plates were returned to the incubator for an additional 22 hours.

BrdU ELISA

After 24 hour exposure to the test compounds, the cells were labeled with BrdU (Roche Biochemicals 1-647-229), by adding 20 µL per well of BrdU labeling reagent that has been diluted (1:100) in serum starvation medium. The plates were then returned to the incubator for 4 hours. The labeling medium was removed by draining the medium onto paper towels. The cells were fixed and DNA denatured by adding 200 µL of fixation/denaturation solution to each well and incubating at room temperature for 45 minutes. The fixation/denaturation solution was drained onto paper towels and to each well was added 100 µL of anti-BrdU-POD and the wells were incubated for 2 hours at room temperature. The antibody solution was removed and the wells were each washed 3–4 times with 300 µl PBS. 100 µL of the TMB substrate solution was added to each well and the wells were incubated at room temperature for 5–8 minutes. The reaction was then stopped by adding 100 µL per well of 1 M phosphoric acid. The plates were read at 450 nm with reference wavelength of 650 nm. The percent inhibition for each test compound was calculated by subtracting the absorbency of the blank (no cells) wells from all wells, then subtracting the division of the average absorbency of each test duplicate by the average of the controls from 1. The final product was then multiplied by 100 (% of inhibition=(1−average absorbency of test duplicate/average of control) 100). The $IC_{50}$ value is the concentration of test compound that inhibits by 50% BrdU labeling, and is a measure of inhibition of cell proliferation. The $IC_{50}$ is determined from the linear regression of a plot of the logarithm of the concentration versus percent inhibition. The $IC_{50}$ values are shown in Table 2 below.

TABLE 2

IC$_{50}$ (μM) of VEGF and FGF-Stimulated HUVEC Proliferation Assays

| Example | HUVEC/VEFG | HUVEC/bFGFR |
|---|---|---|
| 1g | <10 | <10 |
| 4b | <10 | <10 |
| 3 | <10 | <10 |
| 5b | <10 | <10 |
| 6 | <10 | <10 |
| 8d | <10 | <10 |
| 9b | <10 | <10 |
| 10 | <10 | <10 |
| 15b | <10 | <10 |
| 18 | <10 | <10 |
| 19 | <10 | <10 |
| 20b | <10 | <10 |

Example 24

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 25

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 26

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 27

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound of formula:

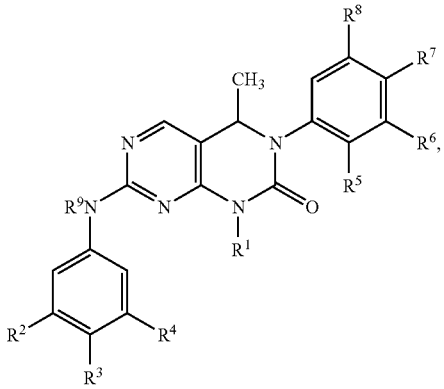

or a pharmaceutically acceptable salt thereof, wherein
$R^1$ is selected from the group
H,
$C_{1-10}$ alkyl,
$C_{1-10}$ alkyl substituted by up to three groups selected from aryl, cycloalkyl, heteroaryl, heterocycle, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$, wherein the aryl, cycloalkyl, heteroaryl, and heterocycle groups may each independently be substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
aryl,
aryl substituted by up to three groups selected from lower alkyl, $NR^{10}R^{11}$, $OR^{12}$, $SR^{12}$, halogen, $COR^{13}$, $CO_2R^{13}$, $CONR^3R^{14}$, $SO_2NR^{13}R^{14}$, $SOR^{13}$, $SO_2R^{13}$, CN and $NO_2$,
heteroaryl,
heteroaryl substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
heterocycle,
heterocycle substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
$C_{3-10}$ cycloalkyl,
$C_{3-10}$ cycloalkyl substituted by up to three groups selected from lower alkyl $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
$C_{2-10}$ alkenyl,
$C_{2-10}$ alkenyl substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$, and
$C_{2-10}$ alkynyl, substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$;

$R^2$, $R^3$ and $R^4$ are independently selected from the group consisting of
H,
halogen,
$CO_2R^{13}$,
$CONR^{13}R^{14}$,
$CONR^{13}R^{14}$,
$SOR^{13}$,
$SO_2R^{13}$,
CN, and
$NO_2$;

$R^5$, $R^6$, $R^7$ and $R^8$ are independently selected from the group
H,
lower alkyl,
lower alkyl substituted by hydroxy or alkoxy,
$NR^{15}R^{16}$,
OH,
$OR^{17}$,
$SR^{17}$,
halogen,
$COR^{17}$,
$CO_2R^{17}$,
$CONR^{17}R^{18}$,
$SO_2NR^{17}R^{18}$,
$SOR^{17}$,
$SO_2R^{17}$, and
CN;

$R^9$ is selected from the group
H,

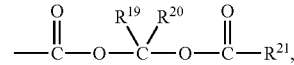

and
$COR^{17}$;

$R^{10}$ and $R^{11}$ are independently selected from the group
H,
$COR^{13}$,
$COR^{13}$
$CO_2R^{13}$,
$CONR^{13}R^{14}$,
$SO_2R^{13}$,
$SO_2NR^{13}R^{14}$,
lower alkyl,
lower alkyl substituted by hydroxy, alkoxy or $NR^{15}R^{16}$,
cycloalkyl,
cycloalkyl substituted by hydroxy, alkoxy, lower alkyl, or $NR^{15}R^{16}$,
heterocycle, and
heterocycle substituted by hydroxy, alkoxy, lower alkyl, or $NR^{15}R^{16}$,
or, alternatively, $NR^{10}R^{11}$ can form a ring having 3 to 7 atoms, said ring optionally including one or more additional hetero atoms and being optionally substituted by the group consisting of one or more lower alkyl, $OR^{12}$, $COR^{13}$, $CO_2R^{13}$, $CONR^{13}R^{14}$, $SOR^{13}$, $SO_2R^{13}$, and $SO_2NR^{13}R^{14}$;

$R^{12}$ is selected from the group
H,
lower alkyl,
$CONR^{13}R^{14}$,
$C_{2-6}$ alkyl substituted by hydroxy, alkoxy, or $NR^{15}R^{16}$,
cycloalkyl,
cycloalkyl substituted by hydroxy, alkoxy, lower alkyl, or $NR^{15}R^{16}$, heterocycle, and heterocycle substituted by hydroxy, alkoxy, lower alkyl, or $NR^{15}R^{16}$;

$R^{13}$ and $R^{14}$ are independently selected from the group
H,
lower alkyl,
$C_{2-6}$ alkyl substituted by hydroxy, alkoxy, or $NR^{15}R^{16}$,
cycloalkyl,
cycloalkyl substituted by hydroxy, alkoxy, lower alkyl, or $NR^{15}R^{16}$,
heterocycle, and
heterocycle substituted by hydroxy, alkoxy, lower alkyl, or $NR^{15}R^{16}$,
or, alternatively, $NR^{13}R^{14}$ can form a ring having 3 to 7 atoms, said ring optionally including one or more additional hetero atoms and being optionally substituted by the group consisting of one or more lower alkyl, $OR^{17}$, $COR^{17}$, $CO_2R^{17}$, $CONR^{17}R^{18}$, $SO_2R^{17}$, and $SO_2NR^{17}R^{18}$;

$R^{15}$ is selected from the group
H,
lower alkyl,
$COR^{17}$, and
$CO_2R^{17}$; and $R^{16}$, $R^{17}$ and $R^{18}$ are independently selected from the group
H, and
lower alkyl,
or, alternatively, $NR^{15}R^{16}$ and $NR^{17}R^{18}$ can each independently form a ring having 3 to 7 atoms, said ring optionally including one or more additional hetero atoms;

$R^{19}$ and $R^{20}$ are independently selected from the group
H, and
lower alkyl; and $R^{21}$ is selected from
lower alkyl, and
$C_{2-6}$ alkyl substituted by hydroxy, alkoxy or NR R
or a pharmaceutically acceptable salt thereof.

2. The compound of claim 1 wherein $R^1$ is selected from aryl and aryl substituted by $OR^{12}$ or $CONR^{13}R^{14}$.

3. The compound of claim 1 wherein $R^1$ is selected from lower alkyl and $C_{2-6}$ alkyl substituted by $OR^{12}$ or $CONR^{13}R^{14}$.

4. The compound of claim 2 wherein $R^2$ is H.
5. The compound of claim 3 wherein $R^2$ is H.
6. The compound of claim 1 wherein $R^3$ is H.
7. The compound of claim 1 wherein $R^2$ and $R^3$ are H.
8. The compound of claim 1 wherein $R^2$, $R^3$ and $R^4$ are H.
9. The compound of claim 1 wherein $R^3$ is halogen.
10. The compound of claim 1 having the formula 11. A compound selected from the group:
(±)-3-(4-Methoxy-phenyl)-4-methyl-1-phenyl-7-phenylamino-3,4-dihydro-1H-pyrimido[4,5-d]pyrimidin-2-one;
3-(4-Methoxy-phenyl)-4-(R)-methyl-1-phenyl-7-phenylamino-3,4-dihydro-1H-pyrimido[4,5-d]pyrimidin-2-one;
3-(4-Methoxy-phenyl)-4-(S)-methyl-1-phenyl-7-phenylamino-3,4-dihydro-1H-pyrimido[4,5-d]pyrimidin-2-one;
(±)-1,3-Bis-(4-methoxy-phenyl)-4-methyl-7-phenylamino-3,4-dihydro-1H-pyrimido[4,5-d]pyrimidin-2-one;
(±)-3-[3-(4-Methoxy-phenyl)-4-methyl-2-oxo-7-phenylamino-3,4-dihydro-2H-pyrimido[4,5-d]pyrimidin-1-yl]-benzonitrile; and
(±)-3-[3-(4-Methoxy-phenyl)-4-methyl-2-oxo-7-phenylamino-3,4-dihydro-2H-pyrimido[4,5-d]pyrimidin-1-yl]-benzamide.

12. A compound selected from the group:
(±)-3-(2-Fluoro-4-methoxy-phenyl)-4-methyl-1-phenyl-7-phenylamino-3,4-dihydro-1H-pyrimido[4,5-d]pyrimidin-2-one;
(±)-3-[3-(2-Fluoro-4-methoxy-phenyl)-4-methyl-2-oxo-7-phenylamino-3,4-dihydro-2H-pyrimido[4,5-d]pyrimidin-1-yl]-benzonitrile;
(±)-3-[3-(2-Fluoro-4-methoxy-phenyl)-4-methyl-2-oxo-7-phenylamino-3,4-dihydro-2H-pyrimido[4,5-d]pyrimidin-1-yl]-benzamide;
(±)-3-(2-Chloro-5-methoxy-phenyl)-4-methyl-1-phenyl-7-phenylamino-3,4-dihydro-1H-pyrimido[4,5-d]pyrimidin-2-one; and
1-(2-Hydroxy-1-(S)-methyl-ethyl)-3-(4-methoxy-phenyl)-4-methyl-7-phenylamino-3,4-dihydro-1H-pyrimido[4,5-d]pyrimidin-2-one.

13. A compound selected from the group:
1-(2-Hydroxy-1-(R)-methyl-ethyl)-3-(4-methoxy-phenyl)-4-(R)-methyl-7-phenylamino-3,4-dihydro-1H-pyrimido[4,5-d]pyrimidin-2-one;
1-(2-Hydroxy-1-(R)-methyl-ethyl)-3-(4-methoxy-phenyl)-4-(S)-methyl-7-phenylamino-3,4-dihydro-1H-pyrimido[4,5-d]pyrimidin-2-one;

3-(4-Methoxy-phenyl)-4-methyl-7-phenylamino-1-[1-(S)-phenyl-ethyl]-3,4-dihydro-1H-pyrimido[4,5-d]pyrimidin-2-one;

(±)-N-[6-(4-Methoxy-phenyl)-5-methyl-7-oxo-8-phenyl-5,6,7,8-tetrahydro-pyrimido[4,5-d]pyrimidin-2-yl]-N-phenyl-acetamide; and (±)-1-(trans-4-Hydroxy-cyclohexyl)-3-(4-methoxy-phenyl)-4-methyl-7-phenylamino-3,4-dihydro-1H-pyrimido[4,5-d]pyrimidin-2-one.

14. A compound selected from the group:

1-[(1R,3R)-3-Hydroxy-cyclopentyl]-3-(4-methoxy-phenyl)-4-(S)-methyl-7-phenylamino-3,4-dihydro-1H-pyrimido[4,5-d]pyrimidin-2-one;

1-[(1S,3S)-3-Hydroxy-cyclopentyl]-3-(4-methoxy-phenyl)-4-(S)-methyl-7-phenylamino-3,4-dihydro-1H-pyrimido[4,5-d]pyrimidin-2-one;

7-(4-Fluoro-phenylamino)-1-[(1R,3R)-3-hydroxy-cyclopentyl)]-3-(4-methoxy-phenyl)-4-(S)-methyl-3,4-dihydro-1H-pyrimido[4,5-d]pyrimidin-2-one;

7-(4-Fluoro-phenylamino)-1-[(1S,3S)-3-hydroxy-cyclopentyl)]-3-(4-methoxy-phenyl)-4-(S)-methyl-3,4-dihydro-1H-pyrimido[4,5-d]pyrimidin-2-one;

7-(4-Fluoro-phenylamino)-1-(2-hydroxy-1-(R)-methyl-ethyl)-3-(4-methoxy-phenyl)-4-(S)-methyl-3,4-dihydro-1H-pyrimido[4,5-d]pyrimidin-2-one;

3-(4-Chloro-phenyl)-7-(4-fluoro-phenylamino)-1-(2-hydroxy-1-(R)-methyl-ethyl)-4-(S)-methyl-3,4-dihydro-1H-pyrimido[4,5-d]pyrimidin-2-one;

3-(4-Chloro-2-fluoro-phenyl)-7-(4-fluoro-phenylamino)-1-(2-hydroxy-1-(R)-methyl-ethyl)-4-(S)-methyl-3,4-dihydro-1H-pyrimido[4,5-d]pyrimidin-2-one;

3-(4-Chloro-phenyl)-1-(2-hydroxy-1-(R)-methyl-ethyl)-4-(S)-methyl-7-phenylamino-3,4-dihydro-1H-pyrimido[4,5-d]pyrimidin-2-one;

3-(4-Chloro-2-fluoro-phenyl)-1-(2-hydroxy-1-(R)-methyl-ethyl)-4-(S)-methyl-7-phenylamino-3,4-dihydro-1H-pyrimido[4,5-d]pyrimidin-2-one;

3-(4-Chloro-phenyl)-1-(3-hydroxy-2-(S)-methyl-propyl)-4-(S)-methyl-7-phenylamino-3,4-dihydro-1H-pyrimido[4,5-d]pyrimidin-2-one; and 3-(4-Chloro-2-fluoro-phenyl)-1-(3-hydroxy-2-(S)-methyl-propyl)-4-(S)-methyl-7-phenylamino-3,4-dihydro-1H-pyrimido[4,5-d]pyrimidin-2-one.

15. A compound selected from the group:

(±)-[1-(2,4-Dichloro-pyrimidin-5-yl)-ethyl]-(4-methoxy-phenyl)-amine;

(±)-7-Chloro-3-(4-methoxy-phenyl)-4-methyl-1-phenyl-3,4-dihydro-1H-pyrimido[4,5-d]pyrimidin-2-one;

(±)-{2-Chloro-5-[1-(4-methoxy-phenylamino)-ethyl]-pyrimidin-4-yl}-(4-methoxy-phenyl)-amine;

(±)-7-Chloro-1,3-bis-(4-methoxy-phenyl)-4-methyl-3,4-dihydro-1H-pyrimido[4,5-d]pyrimidin-2-one;

(±)-3-[7-Chloro-3-(4-methoxy-phenyl)-4-methyl-2-oxo-3,4-dihydro-2H-pyrimido[4,5-d]pyrimidin-1-yl]-benzonitrile;

(±)-[1-(2,4-Dichloro-pyrimidin-5-yl)-ethyl]-(2-fluoro-4-methoxy-phenyl)-amine;

(±)-7-Chloro-3-(2-fluoro-4-methoxy-phenyl)-4-methyl-1-phenyl-3,4-dihydro-1H-pyrimido[4,5-d]pyrimidin-2-one;

(±)-3-[7-Chloro-3-(2-fluoro-4-methoxy-phenyl)-4-methyl-2-oxo-3,4-dihydro-2H-pyrimido[4,5-d]pyrimidin-1-yl]-benzonitrile; and (±)-(2-Chloro-5-methoxy-phenyl)-[1-(2,4-dichloro-pyrimidin-5-yl)-ethyl]-amine.

16. A compound selected from the group:

(±)-7-Chloro-3-(2-chloro-5-methoxy-phenyl)-4-methyl-1-phenyl-3,4-dihydro-1H-pyrimido[4,5-d]pyrimidin-2-one;

1-[2-(tert-Butyl-diphenyl-silanyloxy)-1-(S)-methyl-ethyl]-7-chloro-3-(4-methoxy-phenyl)-4-methyl-3,4-dihydro-1H-pyrimido[4,5-d]pyrimidin-2-one;

3-[2-tert-Butyl-diphenyl-silanyloxy-1-(R)-methyl-ethyl]-1-(R)-[1-(2,4-dichloropyrimidin-5-yl)-ethyl]-1-(4-methoxyphenyl)-urea;

3-[2-tert-Butyl-diphenyl-silanyloxy-1-(R)-methyl-ethyl]-1-(S)-[1-(2,4-dichloropyrimidin-5-yl)-ethyl]-1-(4-methoxyphenyl)-urea;

1-[2-(tert-Butyl-diphenyl-silanyloxy)-1-(R)-methyl-ethyl]-7-chloro-3-(4-methoxy-phenyl)-(R)-4-methyl-3,4-dihydro-1H-pyrimido[4,5-d]pyrimidin-2-one;

1-[2-(tert-Butyl-diphenyl-silanyloxy)-1-(R)-methyl-ethyl]-7-chloro-3-(4-methoxy-phenyl)-4-(S)-methyl-3,4-dihydro-1H-pyrimido[4,5-d]pyrimidin-2-one;

1-[1-(2,4-Dichloro-pyrimidin-5-yl)-ethyl]-1-(4-methoxy-phenyl)-3-[1-(S)-phenyl-ethyl]-urea; and 7-Chloro-3-(4-methoxy-phenyl)-4-methyl-1-[1-(S)-phenyl-ethyl]-3,4-dihydro-1H-pyrimido[4,5-d]pyrimidin-2-one.

17. A pharmaceutical composition comprising a therapeutically effective amount of a compound of claim 1 and a pharmaceutically acceptable carrier or excipient.

18. A method of treating breast, lung, colon or prostate cancer comprising administering a therapeutically effective amount of a compound of claim 1.

19. A method of controlling breast or colon cancer comprising administering a therapeutically effective amount of a compound of claim 1.

* * * * *